(12) United States Patent
Hunter et al.

(10) Patent No.: US 11,001,842 B2
(45) Date of Patent: May 11, 2021

(54) PEPTIDE PHOSPHORODIAMIDATE MORPHOLINO OLIGOMERS PLANT DELIVERY TO REDUCE PATHOGENS AND INSECT PESTS

(71) Applicants: The United States of America, as represented by the Secretary of Agriculture, Washington, DC (US); UNIVERSITY OF FLORIDA, Lake Alfred, FL (US)

(72) Inventors: Wayne B. Hunter, Port St Lucie, FL (US); Kirsten Pelz-Stelinski, Lake Alfred, FL (US)

(73) Assignees: The United States of America, as represented by The Secretary of Agriculture, Washington, DC (US); University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 16/412,735

(22) Filed: May 15, 2019

(65) Prior Publication Data
US 2020/0362335 A1 Nov. 19, 2020

(51) Int. Cl.
*C12N 15/113* (2010.01)

(52) U.S. Cl.
CPC ........ *C12N 15/113* (2013.01); *C12N 2310/14* (2013.01); *C12N 2310/31* (2013.01); *C12N 2310/3233* (2013.01); *C12N 2310/3513* (2013.01); *C12N 2320/32* (2013.01)

(58) Field of Classification Search
None
See application file for complete search history.

(56) References Cited

U.S. PATENT DOCUMENTS

2012/0316220 A1* 12/2012 Ward ................. A61P 31/12
514/44 A
2015/0099791 A1* 4/2015 Krieg ................. A61K 47/64
514/44 A

OTHER PUBLICATIONS

Hunter, Treatments for targeting bacteria and psyllids in citrus trees, meeting presentation at Entomology 2017, Nov. 2017 [retrieved on Aug. 28, 2020] Retrieved from the internet <URL: https://pag.confex.com/pag/xxvi/recordingredirect.cgi/oid/Recording3083/paper30637_1.pdf>.*

* cited by examiner

*Primary Examiner* — Tracy Vivlemore
(74) *Attorney, Agent, or Firm* — John D. Fado; Mark D. McNemar

(57) ABSTRACT

The current disclosure provides for peptide-conjugated phosphorodiamidate morpholino oligomers (PPMOs) antisense oligonucleotides that target plant pathogens and insect pests by targeting the microbes within the insect pest. Methods of delivering PPMOs to bacteria in plants, in insect carriers, and to the insects via plant feeding are also provided.

15 Claims, 12 Drawing Sheets
(7 of 12 Drawing Sheet(s) Filed in Color)
Specification includes a Sequence Listing.

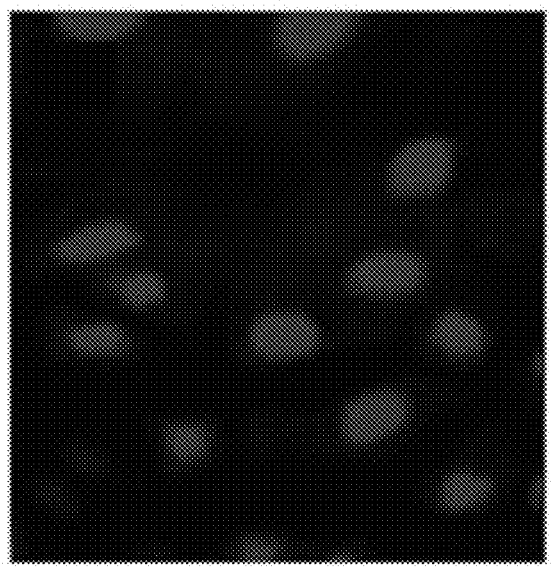 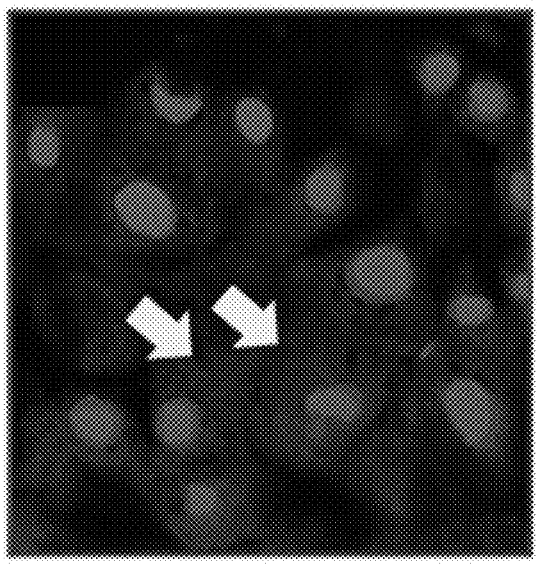
FIG. 6A                    FIG. 6B

SEQUENCE LISTING

```
<160> NUMBER OF SEQ ID NOS: 61

<210> SEQ ID NO 1
<211> LENGTH: 14
<212> TYPE: DNA
<213> ORGANISM: Artificial Sequence
<220> FEATURE:
<223> OTHER INFORMATION: Chemically Synthesized

<400> SEQUENCE: 1
ttaccctgac cgtc                                                         14

<210> SEQ ID NO 2
```

<211> LENGTH: 14
<212> TYPE: DNA
<213> ORGANISM: Artificial Sequence
<220> FEATURE:
<223> OTHER INFORMATION: Chemically Synthesized

<400> SEQUENCE: 2
tttccttgtc cttc                                                       14

<210> SEQ ID NO 3
<211> LENGTH: 14
<212> TYPE: DNA
<213> ORGANISM: Artificial Sequence
<220> FEATURE:
<223> OTHER INFORMATION: Chemically Synthesized

<400> SEQUENCE: 3
gcttagaagg acga                                                       14

<210> SEQ ID NO 4
<211> LENGTH: 14
<212> TYPE: DNA
<213> ORGANISM: Artificial Sequence
<220> FEATURE:
<223> OTHER INFORMATION: Chemicallly Synthesized

<400> SEQUENCE: 4
ttaccttgtc catc                                                       14

<210> SEQ ID NO 5
<211> LENGTH: 14
<212> TYPE: DNA
<213> ORGANISM: Artificial Sequence
<220> FEATURE:
<223> OTHER INFORMATION: Chemically Synthesized

<400> SEQUENCE: 5
ttaccttggc cctc                                                       14

<210> SEQ ID NO 6
<211> LENGTH: 15
<212> TYPE: DNA
<213> ORGANISM: Artificial Sequence
<220> FEATURE:
<223> OTHER INFORMATION: Chemically Synthesized

<400> SEQUENCE: 6
ttttccctgt ccttc                                                      15

<210> SEQ ID NO 7
<211> LENGTH: 15
<212> TYPE: DNA
<213> ORGANISM: Artificial Sequence
<220> FEATURE:
<223> OTHER INFORMATION: Chemically Synthesized

<400> SEQUENCE: 7
ttttccttgt ccttc                                                      15

<210> SEQ ID NO 8
<211> LENGTH: 14
<212> TYPE: DNA
<213> ORGANISM: Artificial Sequence
<220> FEATURE:
<223> OTHER INFORMATION: Chemically Synthesized

<400> SEQUENCE: 8

-continued ttcccctgcc cttc                                          14

<210> SEQ ID NO 9
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 9
ccatctgcat cataccaa                                      18

<210> SEQ ID NO 10
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 10
ttctgctgcc ggaggatc                                      18

<210> SEQ ID NO 11
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 11
aataccgcta ccaatgct                                      18

<210> SEQ ID NO 12
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 12
ctggtactcg aataagag                                      18

<210> SEQ ID NO 13
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 13
gcgtaggaga gataagaa                                      18

<210> SEQ ID NO 14
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 14
atctccatct atcgaacc                                      18

<210> SEQ ID NO 15
<211> LENGTH: 18
<212> TYPE: DNA

```
<210> SEQ ID NO 15
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 15
tccaagcgtt gttgaaag                                                   18

<210> SEQ ID NO 16
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 16
ttcctcatta agtgcgag                                                   18

<210> SEQ ID NO 17
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 17
gcacatctgg taatgctc                                                   18

<210> SEQ ID NO 18
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 18
acacgtctat gaactggt                                                   18

<210> SEQ ID NO 19
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 19
gaatatgagc gtactcac                                                   18

<210> SEQ ID NO 20
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 20
gcctcatacc tataactc                                                   18

<210> SEQ ID NO 21
<211> LENGTH: 14
<212> TYPE: DNA
<213> ORGANISM: Artificial Sequence
<220> FEATURE:
<223> OTHER INFORMATION: Chemically Synthesized

<400> SEQUENCE: 21 tttcctttc ctcc                                                        14
```

<210> SEQ ID NO 22
<211> LENGTH: 14
<212> TYPE: DNA
<213> ORGANISM: Artificial Sequence
<220> FEATURE:
<223> OTHER INFORMATION: Chemically Synthesized

<400> SEQUENCE: 22
ttaccttgac catc                                                       14

<210> SEQ ID NO 23
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 23
catccgtgac gataacca                                                   18

<210> SEQ ID NO 24
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 24
gcaagtacta agtcagct                                                   18

<210> SEQ ID NO 25
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 25
cagatatgcc agtagtga                                                   18

<210> SEQ ID NO 26
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 26
cgaactagta ctcctcca                                                   18

<210> SEQ ID NO 27
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 27
gctcgatctg atgccgaa                                                   18

<210> SEQ ID NO 28
<211> LENGTH: 18
<212> TYPE: DNA
<213> ORGANISM: Artificial Sequence
<220> FEATURE:

<223> OTHER INFORMATION: Chemically Synthesized

<400> SEQUENCE: 28
gtatgacctc ctcgtatt                                              18

<210> SEQ ID NO 29
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 29
gatggtgtta gtccagct                                              18

<210> SEQ ID NO 30
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 30
tgtgtgcatg agcttgtt                                              18

<210> SEQ ID NO 31
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 31
aaggtcttcc tgctaaga                                              18

<210> SEQ ID NO 32
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 32
gatagcgcaa ttacaacac                                             19

<210> SEQ ID NO 33
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 33
tgctcctcat aatcagct                                              18

<210> SEQ ID NO 34
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 34
caatccacca atagatcc                                              18

```
<210> SEQ ID NO 35
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 35
aatgctactc caccacca                                                 18

<210> SEQ ID NO 36
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 36
tctgtagctg cacctact                                                 18

<210> SEQ ID NO 37
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 37
cctcgtgtag aagcttgt                                                 18

<210> SEQ ID NO 38
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 38
acgaggtgct cgtgatgt                                                 18

<210> SEQ ID NO 39
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 39
ccagatcggt gcacaaca                                                 18

<210> SEQ ID NO 40
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 40
cgcatacaaa gatccagt                                                 18

<210> SEQ ID NO 41
<211> LENGTH: 18
<212> TYPE: DNA
<213> ORGANISM: Artificial Sequence
<220> FEATURE:
<223> OTHER INFORMATION: Chemically Synthesized
```

<400> SEQUENCE: 41
tgttgtgcct tctctaac                                              18

<210> SEQ ID NO 42
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 42
ctgcgctatt atatctcc                                              18

<210> SEQ ID NO 43
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 43
gcaatagcat cacaacg                                               17

<210> SEQ ID NO 44
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 44
actcaatgcc tcgattg                                               17

<210> SEQ ID NO 45
<211> LENGTH: 14
<212> TYPE: DNA
<213> ORGANISM: Artificial Sequence
<220> FEATURE:
<223> OTHER INFORMATION: Chemically Synthesized

<400> SEQUENCE: 45
ttaccttgcc catc                                                  14

<210> SEQ ID NO 46
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 46
tagcgacgcc tgattcac                                              18

<210> SEQ ID NO 47
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 47
ctatcagaac ggcatctt                                              18

<210> SEQ ID NO 48
<211> LENGTH: 18

-continued

<212> TYPE: DNA
<213> ORGANISM: Artificial Sequence
<220> FEATURE:
<223> OTHER INFORMATION: Chemically Synthesized

<400> SEQUENCE: 48
ttgcaaagcg acacatgg 18

<210> SEQ ID NO 49
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 49
tagaaatgtt gggagcca 18

<210> SEQ ID NO 50
<211> LENGTH: 2733
<212> TYPE: DNA
<213> ORGANISM: Candidatus Liberibacter asiaticus

<400> SEQUENCE: 50
ttattctgtt gactccgctt catcaactat ctcagattct ctaatgcgtt ctactgatac 60
taccctttca tctttcgcag tagaaaaaat aacaacccct ttggtagcac ggctagcaat 120
tctaatctca ttgactggta ctcgaataag agttccttta tccgaaacaa ggatgatttg 180
atcattatcg ttaactggaa ataccgctac caatgctcct atttcattta tttttgacac 240
atcagttgca cgaatacctt ttccgctacg attagaaata cgaaaatcat aagaagatgt 300
tctcttcccg aatccttttt ctgatacagt taagataaat tgctctttta attttaattc 360
ttgacaacgc tcttccgaaa tattgccctc aacagaagaa tcatttttaa gagaagtaat 420
ttcttccgta tcacctgaaa taagacgacg ttgggcggac atatgtttca tataacaaat 480
tcgttcatca taatccgcat ctgcatgaag aacaattgcc atagaaataa cttgatcacc 540
tttagcaagt gatatgcccc taactccgac agaattacgt cccgcaaata ctcgtatagc 600
agaaatcgga aagcggacac attgtccaag tttagtagtc aacaatatat cattttcttg 660
tgtacaggtt tcaacggaaa gaatctcatc tcttgaatct aatttcatcg caatcttacc 720
actacgattg atttgaataa aatcagaaag tttattacgc cgtacattgc catgcttagt 780
agcaaatacg acatataagt tattccaact cgattcatcc tctggaaaag gcataatcgt 840
tgtgatacgc tcaccttgat ttaaagagag gatattaatc aatgctttcc cgcgcgcttg 900
aggtgatcca ataggtaaac gccatacctt ttctttatac acaaatccta aagaagagaa 960
aaaaagaacg gaagtatgtg tgctcacgat aaatagatcc gtaacgaaat cttcgtcacg 1020
catcaccaca ccggatcgcc ccttaccacc acgacgctgc gcccgataga cagaaagtgg 1080
tactcgtttg acatatccga gatgcgaaac cgtcacgacc atgtcttctc gcacaatgca 1140
atcttcgtct tccatatcta ataaaccctc tacaattcgt gtccgacgag gagtatcaag 1200
ttcatcttta accgatagca gttcctgctt gataataccc agcagacgag atcgcgacga 1260
caaaatgtct aagcactcct taatctctat gccaagacta tttaactcat tacgaatatc 1320
gtctcgaccc aatcccgtca accgcgctaa gcgaagctct agaatagcac gcgtctgtac 1380
ttctgataag tacatcgttc catcactacc tatagtataa cttgaatcat caatcagatc 1440
aattaaatct ttaatatcag aagcgttcca acttctctgc ataagctctc gccgagcagt 1500

```
ttctggatta ggtgaaaaac gaataatacg aacaacttcg tctaaattag ccacagcaat   1560
agccaaacct accaaaacat gagctctatc acgtgcttta ttcaaaagat attttgttct   1620
tcttacaacc acttcctcac gaaaagcaac aaaagccttg agtattccta tgagggtaaa   1680
acgctcaggt ttatatccat tcaaagcaac catattgacg ctaaataaac tttgtaaaga   1740
agtataacga tataattggt tgagaataac atccgcagaa gcacctcgct tcaactcaat   1800
gaccactcga taaccttgac gatccgattc atctcgcaga tctgctatat caactatccg   1860
cttttctcta actaattcag caatcttttc aagcattgcc gctttattaa cctgatatgg   1920
aatctcagta acgacaattt gctcccgatc gcctgatgtt ttttctatgt gactgacccc   1980
tcgtattaca atagatcccc gacccgttgc ataagcattt ttaatgccag tacgtcctaa   2040
gatcaccgct cctgttggaa aatctggacc acgaataatc tccatcaagg catccagatc   2100
aatatcagga ttatcaatta cggccacaca accatcaacc acttctccca aattatgagt   2160
cgggatattg gtagccatgc caacggcaat accgccacca ccattgacca gcacattggg   2220
atatctagca caaagcacaa caggttcttg aaaagagcca tcatagttag ggcggaaatc   2280
aacagtatct ttaccaagat catctagcag aaaatgcgct gctttctgca aacgacattc   2340
agtatacctt tctgctgccg gaggatctcc atcgactgat ccaaaatttc cttgtccttc   2400
aattaacaac aaacgcaaag accagtcctg tgccatacgc gccaatgcgt cataaatggc   2460
agcattacca tgtgggtggt atttacccat cacctctccg gaaatacgtg cgcacttcac   2520
atatttttta ttccattcta cgcccatctg catcatacca aaaagtatac gacgatgaac   2580
aggttttaac ccatctcgca aatcagggat agcacggcct aaaatgacat taattgcata   2640
agtaagataa gaattttgca tttcatctgt tattgaaaca gaagttatgc ccttctcctc   2700
ttcttcatca ctagatataa tatgctcggt caa                                 2733
```

<210> SEQ ID NO 51
<211> LENGTH: 2196
<212> TYPE: DNA
<213> ORGANISM: Candidatus Liberibacter asiaticus

<400> SEQUENCE: 51

```
atgaaaaaac gtcaattgat tccaatcgag gcattgagta tcgaacaagc tagaaaagaa     60
ttatcgtctc ttgaacaaga gatatcatat catgatgatt gttattatca gtattcaaaa    120
cctataatct tagattctga atatgacgca ttaaaaagac gttgtgatgc tattgcacat    180
gcttttcctg atttagcacg ctctgaggat cctaatgggc ctctgaataa aatagggga     240
gaaatgaacc tctccttatt taaagtgact cattctatcc caacattatc attagaaaag    300
atttggaata tcgaagatct tcgtaagttc atcactagaa tttatcgttt ttggcaaaaa    360
aaagatgata acagcatttt ttttactctg gagcctaaaa ttgatgggac aatgattact    420
atacgatatg aaaaaggaaa gtttgtttat gctgctttgc gtggtgacgg tcatagcgga    480
gaggatgtta gtgcttgtat tcgtgctatt ccgacaattc ctcgtgtttt atcattgaat    540
attccagaaa ttatagaagt gcgtggtgaa gtttacatct caaaaaatga ttttcttgcg    600
cttaatgatg aaatgattgc agtcggccga aaaccctatg ctaatcctag aaacgctgct    660
tctggcatat tacgtcgttt aaatcctacg gatattactc ggtatttgaa ttttttttgtg   720
catggattag gaaaaacatc tgagatattc gcaaaaggtc agtatgaaat gctacaaaaa    780
atgcgttgtc taggctttcc tgttaataac ggagttcgac aagcgaatac ttttcacggt    840
atcgtatcct attataatga aatgaaatca atacgttcta ctcttccata tgatatagat    900
```

```
ggattggtat ataaggtcga tgaattttct ttacaaaaac aattaggaga acgagctcga    960
agcccacgtt ggatgatatc gcataaattt gcagagaaac aagcatctac gcgtctttta   1020
gatattgata ttcaaattgg tcgtactggt attctcacgc cggtagctcg tcttgaacct   1080
gttaacatag gaggtgcttt aatcactaat gcaacattgc ataatgaaga ttacatcaaa   1140
ggattggatg catctggtaa agtaatgcgt ggaggaaggg atattcgtgt aggggatagg   1200
gtcttggtca aaagagccgg agaggtgatt cctaaagttg tggatattat tgtcaatgaa   1260
agacatcctg atgctcaacc gttttctttt ccttcttttt gtcctatctg tcagagtcga   1320
gtagtgcgtg atttaaatcc gaaaacagga aaacttgttg ctgcccatcg ttgtacggga   1380
ggacttgcgt gctcggcaca gcaattagaa cgtcttaagc attttgtctc gcgagatgct   1440
ttcaatatag aaggtttagg aaaacaacaa ttggatttct tctttaaatc agaagatcct   1500
gctttttcta ttaggattcc tgccgatatt tttacattgc aacgtcgtca acaaacttct   1560
actacaaaga ttgagaatat tctaggtttt ggcgatgtta gtgtcaccaa tctttacgat   1620
tctattaata aaagacgcaa tatttctttg gaaagattta tattttcctt aggtattcgg   1680
catgttggcg cagaaattgc cagatctttg gcgaaatatt atctctcata tcaaaatttt   1740
gcacaagaaa tcaacaacat tattgcacat aacaatgatg attggctgtc tttaataaga   1800
gttcctctag taggagatat aatagcgcag gctattgtag aattttatca gaatcctagg   1860
aatatttgtg ctgtagaagc actgttaaaa gaagtatctc cttctattgg gcgtcacgaa   1920
aaaaatgtca gctctgagat cgaaaataag aaattagtat ttaccggaac cctgcagaaa   1980
attcaacgcc ataaagcaca agaatatgtg actcagttag gtgctgttgt ttctgctatt   2040
ctttctcgta aaactgatat tattattgtt ggtgataatc ctggttccaa gttagagaag   2100
gcacaacaac taggtgttaa aataatgaac gaagagcaat tttatttctt attacaacag   2160
tataatacaa cgttgcgtat ccacgacgat gactaa                             2196
```

<210> SEQ ID NO 52
<211> LENGTH: 1566
<212> TYPE: DNA
<213> ORGANISM: Candidatus Liberibacter asiaticus

<400> SEQUENCE: 52

```
ctataaaaaa cgaggaaaaa ttggatcgaa tgttttatgt agcatgaatc ctggtttcaa     60
tctttgatct aacgattgaa aacaacgatt ttcatccgca acaaacaaaa tgtcgaaaat    120
tttgtttgcc aatttaggaa caaaagcctg caacaaaatc gcaagttggc gtatgacttc    180
taccgtcaca tacaaaaccg tagatgcacg atcaggattc gtttttttca attcccacgg    240
cttttgtgca tcaaaatatc gatctacttc ggaaacaaga gaaataactt gtgccaatgc    300
tctatgaatc aactgatttt gcatattctc ccgaatctcc tgaaggactc tagaacaaac    360
agataatata ctttcatcag actcagtaaa cgcaccggga gtaggaatca tgccatcata    420
gtcttttaaa atcatagaaa ccgaccgact aacgaggtta ccgataccat tagcaagatc    480
tgcattaacg cgctttttca gaccatcctt atcataaaaa ccatcttttc cacaagcaat    540
ttctcgtacg aggaaatatc gcaacgcatc aacgccgact tcttctatca cttctatagg    600
atcaataaca ttccccaatg atttagatat tttctcccct ttatgaagaa taaatccatg    660
cgaaaaaact ttttttggca aaggcaaatt ggcagacaat agaaaagctg gccaataaat    720
tgcatgaaag cgtaaaatgt ctttgcctat aacatgcaaa tcagcaggcc aaaattttgc    780
```

-continued ttttgatcca tctgggttat ctaaataccc tgttgtagtc aaataattag tcaaagcatc 840
aatccaaacg tacataatat actgcggatc atcaggtatc tttattcccc aatcaaaagt 900
tttacgagaa agagaaagat cttttaaccc tgattttaca aaagaaataa cctcgttgcg 960
tctttcgata ggcaaaatga attctggatg tgattcataa taagagagca acttatcttg 1020
ataggcagac agacggaaaa agtaaccctc ctcttccatc cactgaacag gattatgttg 1080
ggcattatag tactgaccat ctgctccttt ataaacctca tcatcgttgt agtatgcctc 1140
gtcacgcaac gaataccatc cagaataaca acctttataa atatcacctt tatctgatat 1200
ttttttccat aagatacgac atgtatcgtg atgacgtttt tccgttgtac gaataaaatc 1260
atcgtatgaa atatctaaaa catctgccat atcacggaaa ttacgactgt tttgatcaac 1320
gaaaactttt gtcgttacgc cagcattttg tgctgctttt gcaatttttt gtccatgctc 1380
atcggttcct gttgtaaaaa gaacatctaa accatccaaa cgatgaaacc gtgctaaaac 1440
atctgctata atcatctcat aagcatgtcc aatatgtggt tgagcattcg gatatgcgat 1500
agctgtactg atatataatt tctcacgttc ttttatcaca ttaaacaccc cttttaaacc 1560
atacat 1566

<210> SEQ ID NO 53
<211> LENGTH: 513
<212> TYPE: DNA
<213> ORGANISM: Candidatus Liberibacter asiaticus

<400> SEQUENCE: 53
ttaatcgcgt aactgtacta attttgacat ttttttgtt atcatatcac gctttaaacg 60
tgatagatga tctataaata atataccatt tagatgatca agctcatgtt gcaaacaagt 120
tgctaacaat ccatcagcat atataatctg atgttgcgca ttgcaatcca tatatctcac 180
ggttataaaa gccgatcgct ttacatcagc cctataatct ggaatagaca aacagccttc 240
ttgataaaca gaaaaatcat ctgaaaacgt tattatctta ggattaataa aaaccatcgg 300
attcttacga tgagcatgat cctgcaaatc gatgaccact agtctataca aaactccgat 360
ctgaacggca gctagcccaa taccgtcggt ggaatacata acttccaaca tgttgtctat 420
taagttcata atatcggaat tgattttttc tataggacga gatactctcc gtaaaatagg 480
atctggaaaa ataacaagag gttttttac cat 513

<210> SEQ ID NO 54
<211> LENGTH: 1635
<212> TYPE: DNA
<213> ORGANISM: Candidatus Liberibacter asiaticus

<400> SEQUENCE: 54
ttacagagac tggctatata acacagtagc ttggataaaa ctaacaaaaa gcggatgcgg 60
atctaacggt ctactcttta attcaggatg atactgtact cctataaacc aaggatgatt 120
tatatattcc actacttcgg gaagagcatg atctacagaa aatcctgaaa atttcaaacc 180
acaaccctct aatttttccc tataacgcac attgacttca tagcggtgcc gatgacgttc 240
tggaattaaa tcaagaccat agattctaga aattaaagtt tcttctttca aagaaacatc 300
ataagccccc aatctcattg ttgcccctaa atcatccgag ggcaaacgct tttcctgctg 360
atcccctttc atccattcac tcataagcgc aataactggt actcctgcct cagagaattc 420
agtggaacaa gcattaggta ttcctgcaag attacgcgca gcttctataa cagccatttg 480
cataccaaaa caaataccta aaaaaggtat tttattctca cgagcaaatt ttatagcagc 540

```
aattttcccc tcagaaccac gtttaccaaa tcctcctgga acaagaattc catgaacgcc    600
ataaaagtgc tttacaggat cttctttttc taatgtttcc gcatcaatcc atgacaattg    660
tacctttgta taattgctga caccgctgtg acgtagcgct tctattaaag atctataagc    720
atccttaaga tgaatatatt ttccaacgat agcaactttc acctcattct tcagcgataa    780
agtacgatca caaaaagtct gccaattatc tatttgagga agtgagacat tttcaatgcc    840
aaaagcattt aaaacgacac tatctattcc ctcacggtga tatgaaagtg gaactttata    900
aatatcatca acatcaagcg ctggaatcac agccgacatc ggaacgttac aaaataaaga    960
aatcttacga cgctccatct caggaatatc ccgatcagca cgtattaata aaatatccgg   1020
atgtacacca agagcttgca gttccttaac agaatgttgc gtgggctttg ttttcaactc   1080
cccagaagac ctgatatatg gcataagagt taaatgaata tataaagctt tactaccacg   1140
atgtgaaaat tcattcccaa actgccggat agcttccaca aaaggcatga cttcaatatc   1200
accaatagtt ccaccaatct cacaaataac aaaatcagcg tcttcatttc cttgagtgat   1260
aaactctttt atttcattgg taacatgagg aataacttgt acagttgtac cgagataatc   1320
tcctcgacgc tctctatcta tcacattctt ataaatacgt ccggcagtaa tattgtctgc   1380
tttagcggta gaaattccca taaaacgttc gtaatgacca aaatctaaat ccgcttctcc   1440
accatcatct gtgacaaaaa cctcaccatg ttgtactgga ctcattgttc caggatcaga   1500
attaagataa ggatcaagct tacgcactct cactttatat ttatgtgcct gtaacaatgc   1560
acctagcgat gctgcagcca ctcctttccc caaagaagaa actactccac cagtgataaa   1620
aatatactta accac                                                    1635
```

<210> SEQ ID NO 55
<211> LENGTH: 1329
<212> TYPE: DNA
<213> ORGANISM: Candidatus Liberibacter asiaticus

<400> SEQUENCE: 55

```
atgaaacgta aacgtcttgc tattgtgctt gctgcaggta gagggcatcg tatgaagtct     60
tcttcctcta aggtgttaca gaaaattgct gggaaaccta tgatttccca tgttatggaa    120
accatcgctg cagcaggtat tgaaaacgtt gctttggttc taggatatgg agcagaagaa    180
attacaagga ttaattttcc tcctacgtta tcagtcgagt attatattca agattgccaa    240
caagggactg cacatgccgt tttgacagca caggatgcta taaagccagg atacgatgat    300
gttattatca tgtatggtga tgtaccactg gtttcttctc atactttgaa aaaagcaatg    360
gataaaatag cccaaggata ttctatcgca gtcgttggat ttaatgcgga taatcctaag    420
ggatatgggc gtttattgat aaaaaataat gaaataatag ctattcgtga agaaaacgat    480
gctacagatg aagaaagaaa aattcattat tgtaatagtg gattaatggc tattgatggc    540
ttgtatatca tggattggct tctccaaatt aagaaaaaca aagtatcaca ggagtactac    600
ctcacagata ttattgaaaa agcacgattg gatgggaaaa gtattgcgag tattgatgtt    660
aaggaacaag aagtatgcgg ttgtaataat cgttatgagt tgtctttaat cgaaaacatc    720
tggcaatcac gttatcgtcg ccagatgatg atatcaggtg tgacaatgat cgctccagaa    780
acagtgtttc tttctcacga tactattatt caaccagata ctgtcattga accgcatgtt    840
tttttcggat gtggtgtcag cattgaaaat tatgtacaga tacgtgcatt ttcatattta    900
gaaggagtac atattggtaa aaaaaccatt atcggtcctt ttgctcgtat aagacaggaa    960
```

```
actacaatag aaaaaaatgt ccggatagga aattttttgtg aggtaaaaaa ggctactatt    1020
aaagaaggaa gtaaaattaa tcacctcagt tatgtcggcg atagtgtagt agggaaaaat    1080
gttaacatag gagcaggtac tattacctgt aattatgatg gtacccataa atataaaacg    1140
catataaatg agaatgcttt cataggatct aattcttctt taatcgctcc tattactatt    1200
ggtcaaggta cttatgtagc atctggaagc attattacgc aagatactcc ggaaaattcg    1260
ctcgtattcg ctcgatctcg gcagattgtc aaggaagatg gtgctttgtc aatgcgaaaa    1320
aaaaagtag                                                            1329

<210> SEQ ID NO 56
<211> LENGTH: 617
<212> TYPE: DNA
<213> ORGANISM: Diaphorina citri

<400> SEQUENCE: 56
ttactgccat gattgtgaac caaaaaataa aaagcatttt aacatggtcc tcaatgtttc      60
tctgttacag catgtgatgg cagaaatgcg acaagaatgt aaatgtcacg gcatgtctgg     120
atcttgtact gtcaagacct gctggatgag gcttcctaac ttcagagtta ttggagatgc     180
cggtttgacg gcgcgtccag agtgatggtc agtaatgaag gtaacgttcg tggcagcagt     240
gtggggaaga aaagtcggta caacttccag ctgaatccgt acaatcctga acacaaacct     300
ccaggtgtga aggatttggt ctacctggaa acctcgccag gattctgtga agaatccc      360 gcactgggaa tacagggcac gcatggacga caatgcaatg acaccagtat tggtgtagat     420
ggttgtgatc tgatgtgctg tgggcgaggc tacagaacac aggagatcac cgtcgtggaa     480
cggtgtgctt gtgcttttat ttggtgctgt gaggtcaaat gtaaaacatg tagaacaaag     540
aaaaccattc acacttgctt gtagataatc attattatta atattattag tgattccaga     600
actgtgccta ttgatcc                                                   617

<210> SEQ ID NO 57
<211> LENGTH: 2682
<212> TYPE: DNA
<213> ORGANISM: Xylella fastidiosa

<400> SEQUENCE: 57
atggcagaga ccgccaagga aatcatcaag gtcaatctgg aagacgagat gcgtaagagc      60
tacctcgatt atgcgatgag cgtaatcgta ggtcgtgcac tccccgatgc tcgcgatggc     120
atgaagcctg tgcatcgccg cgtcctgtac gccatgcatg aacttggtgc tcacagcgac     180
aagtcctact tcaaatcggc acgtatcatc ggtgaagtgc tcggtaagta ccatccgcat     240
ggtgatcagt ctgtttacga caccctggta cgtatggcgc aacccttctc gttgcgttac     300
ttactggtag agggccaagg taactttggt tcggtggacg gcgatcctgc cgccgcgatg     360
cgttacaccg agtcccgcat gtcgcggatc agccacgacc tgatggctga catcgataaa     420
gagaccgtcg actttcagcc caattacgac gaaaaagaaa cggaaccaac ggtcatgccg     480
acccggttcc cgaatctatt ggtcaatgga tcgtccggga ttgcagtggg catggccacc     540
aatatcccgc cccataaccc tcgtcgaatcc atcaacgctt gcattgccct tattgataat     600
ccagaactgg atgtcgatgg attgatggaa tatatcccg gtccggattt ccccaccgcc     660
ggcatcatca acggcaccgc tgcattgtt gctggctacc gtaccggtcg tggtcgcgtc     720
cgcatgcgtg ccaaggcgga tattgaagtg gccgacaatg gccgtgaagc catcgttgtt     780
actgagattc cttaccaagt caacaaagca cgtttgatcg aaaaaaattgc tgagttggtg     840
```

```
aaagaaaaga gaattgatgg catcagcgaa ttgcgtgatg aatccgacaa agacggcatg    900
cggatttata tcgaaatcaa acgtggcgag tcggctgagg ttgtcctcaa caacctctac    960
caacagaccc agatggagtc ggtattcgga attaacatgg tggcactggt tgacggccgc   1020
ccccaactac tcaacctcaa acagatactg caagccttca tccgtcaccg ccgcgaagtg   1080
gtcacccgcc gcaccatctt cgaactgcgc aaagcccgtg cccgtgccca cgtcctggaa   1140
ggtttgacgg ttgccctggc caacattgac gagatgattc acctgatcaa acctcgcca    1200 agcccacaag aagcaaaaga gcgcctgctc gccaaaacct gggcacctgg attggtcggt   1260
acattgctca gtgcctcagg tggtgaagca tcgcgcccgg aagatctccc gcaaggcgtg   1320
gggctgattg gcgattccta tcaactgacc gaagtccaag tacggcagat tttggaaatg   1380
cgcctgcacc gcctcaccgg actgaacag gacaaacttg ccgaagagta ccagcagctg   1440
ctagagatca ttgtcggcct gatccgcatc ttggagaacc cggatgtcct attacaggtc   1500
attcgcgatg aactcctcaa gatacgtgaa gaatatggcg atgtacgccg taccgagatc   1560
cgccatagcg aagaagacct agacatcctc gacctcattg caccggagga tgtcgtcgtc   1620
accctgtccc acgccggcta tgccaagcgt cagcctgtgt ccgcctaccg tgcccaaaag   1680
cggggagggc gtggccgcgc tgctgtgacc acaaaagaag aagacttcat tgaccatctc   1740
tggctggtca cacccacga caccctgttg accttcacca gcaccggcaa agtattttgg   1800
ctgtctgtgt accaattgcc agaagccggc tccaacgccc gaggtcgccc catcatcaac   1860
tggatcccct tggagccagg cgaaaaagtg caggccgtcc ttcccgtacg cgaatacgct   1920
gagaaccact atgtgttttt tgccacccgc caagggaccg tcaaaaagac tcccttgagc   1980
gaatttgcat ccgcttagc gcgcggcaaa atcgcgatca accttgatca aggagatgcc   2040
ctgattggtg ttgctctgac cgatggcgaa cgtgatgtcc tgctctttgc ctccaatggc   2100
aagaccgtgc gtttcagtga aacactgtc cgctcaatgg gccgcaccgc cacgggcgtg   2160
cgcggtatca aactgaccga aggagaagag gtggtcagcc tcatcattgc cgaaccggca   2220
actggtgtgg atatgctcga agaagcgaa gaaacggcag atgacgacat ccagacagcc   2280
aacactgccg acagcgtgca cattgatccc acccaggatg catcctctg catcctgacc   2340 gccactgaaa acggctacgg caaatgtacc ccctggctc attaccctcg taaaggccgt   2400
ggcactcaag gcgtcattgg tatccagacc accgagcgca atggccgcct ggttgctgcc   2460
gtcctattag gtgccaccga cgaagtccta ttgatctctg atggcggcac cttggtacgt   2520
acccgtggct ccgagatttc gcgcgttggc cgtaatacc aaggcgtcac cctcatccgc   2580
ttatccaatg gtgaaaaact tcaggcagtc gagcgtctgg atgcttcctt gagtatcccg   2640
gatgagacag aggacgatcc cggcaccgta caccctgcct ga                      2682
```

<210> SEQ ID NO 58
<211> LENGTH: 2703
<212> TYPE: DNA
<213> ORGANISM: Wolbachia sp.

<400> SEQUENCE: 58

```
atgcaagaca atatagtacc agtttcgata gtaaaagagc tagaagattc ttatctctcc     60
tacgcaatga gtgtaatcat aagccgagct ataccgacg tgcgagatgg atttaaacct    120
gtacataggc gtatattata tgcaatgtca agagctgggt tcgatgcagg taagccatat    180
aaaaaggcag ctcgtatagt tggagatgta atgggaaaat atcacccaca tggtgatgca    240
```

```
gctatttacg attccttggt caggatggct caagattttt ctcttctttt accacttatt    300
gatgggcaag gtaactttgg ttcgatagat ggagatccgc cagcttcaat gcgatataca    360
gaagcaaggc tccacagggt gtcgcatttt ttactgaatg atattgatga agatacagtt    420
gattttaggg caaactacga cggaaatgaa acggagcctg tcgtattgcc ggcagaattt    480
cctaatctgt tggtaaacgg tggaagtggt gttgcagttg gtatggcaac caatattcct    540
tctcataatc ttggtgagat aattgatgct gcatgttat atatagataa ccctgaagtt    600
actctagatg agttgcttga agtaatacca gggccggatt ttccaacggg aggaataatt    660
cttggcagat ctggaataag atcagcgttt gctaaaggcc gaggttcaat tgtcgttcag    720
ggtaaaactc atatagaaaa tctgccacaa gatagacaag caatagttat tgatgaaata    780
ccttaccaag taaataaagt aaaattaatt gagaaaatag cgagctcgc aaaagaaaaa    840 agaattgagg gcataacaga gattagggat gagtctgata agtctggtat tagagtagta    900
attgatctca aaaaaacac tgaagcagat tttatattga atcaaatact aggacttact    960
cctctgagaa gtagctttag tgttaatact ttagttctga caacaacag gcctgctttg   1020 atgtcattga agaaatcat agctgctttt attgactta gaaagaagt actaatcagg   1080 agaacagagt ttcgtctaaa aaagacgaga gaaaagctc atatatacat agggctctac   1140
attgcggtcc tcagcataga tgaagtgata aaaatcatcc gtggtgcaaa agatcctgaa   1200
gaagcaagca gagagctttt aaacaaggaa tggaaaacct cagctgaaat aaacacgatt   1260
attgaattaa tctcagacag tatgagcttt ttgaaagatg gagtgtatag attaactgag   1320
ctgcaaacaa aagctattct tgatatgaaa ttgcaacgct taacaggcct tgaaaaaagc   1380
aaattagaaa atgagttaaa ttcaatgctt agcctgataa agaatatat cgcttttctt   1440 ggctcagaag agaaattgat gcaagaaata aaaaacaatt tacaagaaat aaagaataga   1500
tttgccgtac ctcgaagaac ttcaatagaa gaatcagaca tggacattga agctgaagat   1560
ctaattccac aagaagatat ggtagtgacc gtaactatga atggttacat caaacgtgtg   1620
aagctctctc actatagaac ccagcatcgt ggtggaaaag gaaagctagg acagggatta   1680
aaagaggagg acgtaatcac aaaattattt gttggaaata ctcatactag ccttttattc   1740
ttttctaata tcggtcgagt ttacagatta aaagtttaca aactgcctct tgcagagcca   1800
actgcacgtg gaagagcgct tgttaatata ttcccgctta gcgatggtga aactataact   1860
aacatcatgc cgcttccaag tgagaatgac gaaaatcaaa atatagtttt tgctactgct   1920
catgggaaca taaggcgtaa ctccttagcg gattttcact atattccaag caatggaaaa   1980
atagcaataa agctcgatga aggggataaa ttagtgtcag ttaaagtatg tagcgaaatt   2040
gatcacgttc tactttcaac aacgcttgga aaaagcatta gatttgttgt aagcgatgtg   2100 cgtcaatta agagtcgcaa ttcagatgga gtaagaggta tcaaacttgc aaaaaatgac   2160
agcgtgatat ccacgaccat actaaacggc ataggtattg caacagaaac aaaagaactt   2220
tacttaagag ttccgcttgc aaaaaggatg gaagctgcaa ccaataactc aattgattct   2280
aaatcagaaa aaactttgaa tgatttagga ataaagaacg aattattctc aaaactcgca   2340
cttaatgagg aattcatatt aactattact gaaaatggct ttggtaaaag aacttctgca   2400
tatgaatata gggtaacagg tagaggtggt gttggtatta caaatatcct tactactagt   2460
agaaatggca atgttgttgc tagttttcca gttgagcagg atgacaacat aatgcttatt   2520
acagataaag gaaagttaat tcgcatttcg gttaatgaaa ttagaattgc aggacgcagc   2580
actcagggag ttactctgtt taaaacagaa aataaagaaa aggtggtatc ggtagcaaaa   2640
```

| | | |
|---|---|---|
| attgaagatc ctagctccac tgaagagaat atgcctgagg ttgaaagtgc tacttcttct | 2700 | |
| taa | 2703 | |

<210> SEQ ID NO 59
<211> LENGTH: 2713
<212> TYPE: DNA
<213> ORGANISM: Candidatus Liberibacter solanacearum

<400> SEQUENCE: 59

| | |
|---|---|
| ttgaccgagc atattgtacc caatgatgaa gagggtgaga agggcataac ttctgtttcg | 60 |
| atagttgagg aaatgcaaaa ttcttacctt acctatgcaa taaatgtcat tttaggccgt | 120 |
| gctatacctg atttgcgaga tggtttaaaa tctgtccatc gtcgtatact ttttggtatg | 180 |
| atgcagatgg gggtagagtg gaataagaaa tatgtgaagt gtgcgcgtat ttctggagaa | 240 |
| gtgatgggta ataccatcc acacggtaat gctgcgattt acgatgcttt ggcacgtatg | 300 |
| gcacaggatt ggtcattgcg tttattgttg attgaagggc aggggaattt cggctcaatt | 360 |
| gatggagatc ctccggcagc ggaaaggtat actgaatgtc gtttgcaaaa agcggcacat | 420 |
| ttttgctgg atgatctggg caaagataca gttgattttc gtcctaacta tgatggttct | 480 |
| tttcaagagc ctgttgttct tgtgctaaaa tttcctaact tacttgtaaa tggtgctggt | 540 |
| ggtatagccg ttggtatggc gacgaatatt cccacccata atttgggaga ggtgattgag | 600 |
| ggttgtatag ctttaattga taatcctgat attgatcttg atgatatgat gaagattatt | 660 |
| cttggtccag attttccgac aggggctatc attttagggc gttctggaat tagaagtgct | 720 |
| tatgcaacag gtcgaggatc tatcgtaata cgaggcgtta ctcacataga aaaaacagaa | 780 |
| ggtgatcgag aaaagattat cgttactgag atcccgtatc aggtaaataa atcagcaatg | 840 |
| ctggaaaaga ttgctgagtt agttagagaa aagcgtatag tagatatatc agatctgcga | 900 |
| gacgaatcag atcgtcaagg ttatagagta gtcattgagt tgaagcgagg tgcttctgct | 960 |
| gatgttattt taaaccaatt gtaccgctat acttctttac aaagtttgtt cagcgtcaat | 1020 |
| atggttgctt tgaatggata taaacctgag cgatttaccc tgatagaaat cctcaaaaat | 1080 |
| tttattgctt ttcgtgaaga agttgtaggc agaagaacaa aatatctttt gaacaaggca | 1140 |
| cgtgataggg ctcatgtttt agttggtctt gctattgctg tttctaattt agatgaagtg | 1200 |
| gtgcgtatta ttcgttttt tccaaatcca gaatctgctc gacgagagct gatgcagaga | 1260 |
| aattggaatg ctgtagatat taaagatttg atcgatctta ttgatgattc cagctatact | 1320 |
| ataaatagtg atggaaagat gtatctatca gaagttcaaa cgagagcgat tttagaactt | 1380 |
| cgtttagcac gactgacggg gttaggacga acgatattc gcgatgaatt gaatagtctt | 1440 |
| ggtacagaaa ttaaggattg cttagagata ctatcatcac gatcccgttt gttgaatatt | 1500 |
| atcaaacaag aattgaaatt tattaaagat gaacttgata ctcctcgtcg gacagagatt | 1560 |
| gtagatggtt tgttggatat ggaagacgaa gattgtattg tgcagaagaa tatggttgtg | 1620 |
| acggtttcgc attttggata tgtcaagcgt gttccacttt ctttatatcg agcacagcgt | 1680 |
| cgcggtggga aagggcgttc tggcgtagta cacgtaatg aagatttgt aacggatttg | 1740 |
| tttatcgtga atacacatac accagtttg ttttttttcgt ctttaggatt cgtttataag | 1800 |
| gaaaaagtat ggcgtttgcc tattggatcc ctcaatctc gtggaaaggc tttaattaat | 1860 |
| attctttctc tgcaacaggg agaacgcatt acgacgatta tgcctcttcc agaagatgaa | 1920 |
| tcgagttgta gtgatttata tgttgtgttt gctactaaac ttggaaatgt tcggcgtaat | 1980 |

```
aagctctctg attttgttca ggtaaatcgt agtggtaaaa ttgctatgaa attagatgaa      2040
ggggatgaga ttctttctgt tgaaacctgt atggagggaa atgacgtatt actaactact      2100
aagttagggc aatgtattcg atttgcaatt actgatgtgc gagttttttc agggcgtaat      2160
tcagtggggg taaggggaat agttcttgca gaagatgatc aggtgatctc tatggcgatt      2220
gttctccatg ctgatgcaga ttatgatgag cgcgtttgtt atatgaagta tatggcttct      2280
catcgtcgtc ttattgcaag tgatattgat gaaggtggtg ttcttaaaaa tgattcttct      2340
attgaaggga agatttcgga agagcgttgt aaagaattaa agtcaaaaga acaatttatc      2400
ttgaccgtat cagaaaaagg atttggcaaa agaacatctt cttatgattt tcgtatttcc      2460
agtcgtggcg ggaaaggtat tcttgctact gatacttcaa aaatggatga ataggacca      2520
ttgatatcag catttcccgt taatgataag gatcaaatca tactagtttc tgataaagga      2580
actcttattc gagttcctgt taatgatatt agaattgcta gccgttctac aaagggagtt      2640
gttatttttt ctactgcgaa ggatgagaga gtggtatcag ttgagcgtat tagtgaatct      2700
gatattattg atg                                                        2713

<210> SEQ ID NO 60
<211> LENGTH: 2544
<212> TYPE: DNA
<213> ORGANISM: Baumannia cicadellinicola

<400> SEQUENCE: 60
atgagcgagc ttgctaaagc taacaaaata ctgataccag taagtataga agaagaactc       60
aagcgttctt atctagatta tgctatgtca gtaattatag acgtgcatt accagatgtt      120
agagatggac taaaaccagt gcaccgtcgt gtttttatttg ctatgagcat actaggtaat      180
gattggaata aaccttataa aaaatctgca cgtatagtag gcgatgtcat tggaaaatat      240
cacccacata gtgatacagc tgtttatgat gctatagtac gtatggcaca gacattttct      300
ctacgttata tgttagttga tggtcaaggt aattttggtt ctattgatgg agattcagct      360
gctgcaatgc gctatacaga agtgcgtatg tcaaaaattg ctcatgaatt gcttatagat      420
ctagaaaaag atactgttaa ttatgttcct aactatgata gtactgagca aattcccgaa      480
gttatgccaa ctagaatgcc aaatatatta attaatggat cttctggtat agcggtgggg      540
atggctacta atattcctcc acataatctt tttgaaatta tagatgggtg cttagcatat      600
attgatgatg ataaaattag tatcgaagaa ttaatgaaat atattcctgg tccggatttt      660
cccactgcag ctattatcaa tggtaagcaa ggtattgaag aagcatatcg gacaggccgt      720
ggtaaaatat gtattcgtgc acgagccata gtagaagtag aagcaaatac tggccgtgaa      780
attattgttg taagtgaaat tccttatcag gttaataaag ctcgtctaat agaaaaaata      840
gcggatctta ttaaagaaaa acgtatagaa ggaattagtg ttttacgtga tgaatctgat      900
aaagatggaa tgcgtattat tattggcatt aaacgtgatg ccgtcgcaga agtagtactt      960
aataatctat attctatgac tcaattacag gtatcattta gtatcaatat ggtagcgcta     1020
aataatgggc aacctaagat tttttcgctg aaagagatac tctcagcttt tatttgtcac     1080
cgacaggata taattactcg taggactatt tttgaattac gtaaagctcg cgagcgtgtt     1140
catatttttag aagctttggt agttgcacag gcaaacatcg agtctatcat taccttaact     1200
cgtaatgcaa atacaccagt agaagctaag gataaaattat taattagtgc ttggaatcta     1260
ggtaccattg catctatgca atgtcgtgaa gttcatcata tggtacgtcc agaatggtta     1320
gaagaaaaat atggtattca tgatgggagg tactatttaa ccgaaaagca agtacaagct     1380
```

-continued

| | |
|---|---|
| attcttgatt tgcgcctata taatttaact agcttagaat attctaagct tatgatagag | 1440 |
| cacaaagaac tcttaactaa aatagttgat cttcttcgca tattaaatga accagaacgc | 1500 |
| ctcatggaag ttattcgcga agaattaaat tacattcaaa aacagtataa agatcctcgt | 1560 |
| cgtactgaaa ttacaactat atcatccaat ttagtaatag aggatatgat taataaggaa | 1620 |
| aatgttgtcg taactctttc ttaccaaggt tacgtaaaat atcaacccct aaatgactat | 1680 |
| gatgcgcaga aacgaggagg aaaaggaaaa tctgcagtta agatgaagga agaagatttt | 1740 |
| atccatagtt tactcgttgc taatacccac gatactatct tactttttctc tagccgtggt | 1800 |
| cgaatgtatt ggatgaaagt atatcaacta ccagctgcta gccgcggttc acgtggtcgg | 1860 |
| ccaatcgtaa atctactacc attagaaact aatgagcgta ttactactat tcttccagta | 1920 |
| cgtcagtacg aggaaggttg caatgttttc atggcaactg ctagcggtac tgtaaagaaa | 1980 |
| acagctctga tagcatttag tcgtccacgt agcgctggta ttatagcagt taatctgcat | 2040 |
| gaaggtgacg agttaattgg agtaaatgta actaatggta caacgaagt aatgttattt | 2100 |
| tcagcgtatg gtaaagtagt acgtttcccc gaaactcagg tacgtagtat gggtcgtacg | 2160 |
| gcaacaggtg tgcgaggtat taacctcgca gaaggtgata gagtcgtttc actaattata | 2220 |
| ccaaatatag atggtcatat ccttactgta actcaacatg gttatggtaa gcgaacaacc | 2280 |
| cagaacgaat atcctactaa atcacgtgca actcaaggtg ttatatcgat caaagcaagt | 2340 |
| gaacgtaacg gtcaggttat aggtgctatt caagttgatg aacatgatca gattatgctt | 2400 |
| attactgatg ctggcactct agtacgtact agagtttctg aagttagtat cgttgggcgt | 2460 |
| aatactcaag gtattacgct gattcgtact gctgaaaatg agcatgtagt tggcctacaa | 2520 |
| cgtatagctg aacctattga ctaa | 2544 |

<210> SEQ ID NO 61
<211> LENGTH: 2940
<212> TYPE: DNA
<213> ORGANISM: Escherichia coli

<400> SEQUENCE: 61

| | |
|---|---|
| atgagcgacc ttgcgagaga aattacaccg gtcaacattg aggaagagct gaagagctcc | 60 |
| tatctggatt atgcgatgtc ggtcattgtt ggccgtgcgc tgccagatgt ccgagatggc | 120 |
| ctgaagccgg tacaccgtcg cgtactttac gccatgaacg tactaggcaa tgactggaac | 180 |
| aaagcctata aaaatctgc ccgtgtcgtt ggtgacgtaa tcggtaaata ccatccccat | 240 |
| ggtgactcgg cggtctatga cacgatcgtc cgcatggcgc agccattctc gctgcgttat | 300 |
| atgctggtag acggtcaggg taacttcggt tctatcgacg gcgactctgc ggcggcaatg | 360 |
| cgttatacgg aaatccgtct ggcgaaaatt gcccatgaac tgatggccga tctcgaaaaa | 420 |
| gagacggtcg atttcgttga taactatgac ggcacggaaa aaattccgga cgtcatgcca | 480 |
| accaaaattc ctaacctgct ggtgaacggt tcttccggta tcgccgtagg tatggcaacc | 540 |
| aacatcccgc cgcacaacct gacggaagtc atcaacggtt gtctggcgta tattgatgat | 600 |
| gaagacatca gcattgaagg gctgatggaa cacatcccgg agccggactt cccgacggcg | 660 |
| gcaatcatta cggtcgtcg cggtattgaa gaagcttacc gtaccggtcg cggcaaggtg | 720 |
| tatatccgcg ctcgcgcaga agtggaagtt gacgccaaaa ccggtcgtga accattatc | 780 |
| gtccacgaaa ttccgtatca ggtaaacaaa gcgcgcctga tcgagaagat tgcggaactg | 840 |
| gtaaaagaaa aacgcgtgga aggcatcagc gcgctgcgtg acgagtctga caaagacggt | 900 |

-continued

```
atgcgcatcg tgattgaagt gaaacgcgat gcggtcggtg aagttgtgct caacaacctc    960
tactcccaga cccagttgca ggtttctttc ggtatcaaca tggtggcatt gcaccatggt   1020
cagccgaaga tcatgaacct gaaagacatc atcgcggcgt tgttcgtca ccgccgtgaa    1080
gtggtgaccc gtcgtactat tttcgaactg cgtaaagctc gcgatcgtgc tcatatcctt   1140
gaagcattag ccgtggcgct ggcgaacatc gacccgatca tcgaactgat ccgtcatgcg   1200
ccgacgcctg cagaagcgaa aactgcgctg gttgctaatc cgtggcagct gggcaacgtt   1260
gccgcgatgc tcgaacgtgc tggcgacgat gctgcgcgtc cggaatggct ggagccagag   1320
ttcggcgtgc gtgatggtct gtactacctg accgaacagc aagctcaggc gattctggat   1380
ctgcgtttgc agaaactgac cggtcttgag cacgaaaaac tgctcgacga atacaaagag   1440
ctgctggatc agatcgcgga actgttgcgt attcttggta gcgccgatcg tctgatggaa   1500
gtgatccgtg aagagctgga gctggttcgt gaacagttcg gtgacaaacg tcgtactgaa   1560
atcaccgcca acagcgcaga catcaacctg gaagatctga tcacccagga agatgtggtc   1620
gtgacgctct ctcaccaggg ctacgttaag tatcagccgc tttctgaata cgaagcgcag   1680
cgtcgtggcg ggaaaggtaa atctgccgca cgtattaaag aagaagactt tatcgaccga   1740
ctgctggtgg cgaacactca cgaccatatt ctgtgcttct ccagccgtgg tcgcgtctat   1800
tcgatgaaag tttatcagtt gccggaagcc actcgtggcg cgcgcggtcg tccgatcgtc   1860
aacctgctgc cgctggagca ggacgaacgt atcactgcga cctgccagt gaccgagttt    1920
gaagaaggcg tgaaagtctt catggcgacc gctaacggta ccgtgaagaa aactgtcctc   1980
accgagttca accgtctgcg taccgccggt aaagtggcga tcaaactggt tgacggcgat   2040
gagctgatcg gcgttgacct gaccagcggc gaagacgaag taatgctgtt ctccgctgaa   2100
ggtaaagtgg tgcgctttaa agagtcttct gtccgtgcga tgggctgcaa caccaccggt   2160
gttcgcggta ttcgcttagg tgaaggcgat aaagtcgtct ctctgatcgt gcctcgtggc   2220
gatgcgcaa tcctcaccgc aacgcaaaac ggttacggta aacgtaccgc agtggcggaa   2280
tacccaacca gtcgcgtgc gacgaaaggg gttatctcca tcaaggttac cgaacgtaac   2340
ggtttagttg ttggcgcggt acaggtagat gactgcgacc agatcatgat gatcaccgat   2400
gccggtacgc tggtacgtac tcgcgtttcg gaaatcagca tcgtgggccg taacacccag   2460
ggcgtgatcc tcatccgtac tgcggaagat gaaaacgtag tgggtctgca acgtgttgct   2520
gaaccggttg acgaggaaga tctggatacc atcgacggca gtgccgcgga aggggacgat   2580
gaaatcgctc cggaagtgga cgttgacgac gagccagaag aagaataatt ttacttcttc   2640
atgccaaaag ggagctatct cccttgtttg aattgaaaag tccaggctgc aaagtctggg   2700
cttttgtcgt attagggcac ggtaaagttt ggctgtgccc gtaaaaaatg ctggctata    2760
cacaaggaat gtggcaatga gtggtgaaaa aaaggcgaaa ggctggcggt tctatggtct   2820
tgtaggtttt ggcgcaatag cactgctttc cgctggcgtc tgggcgttgc aatatgctgg   2880
cagtgggcca gaaaaaacgt tgtcgccgct ggtggtgcac aacaatctgc aaatcgatct   2940
```

PEPTIDE PHOSPHORODIAMIDATE MORPHOLINO OLIGOMERS PLANT DELIVERY TO REDUCE PATHOGENS AND INSECT PESTS

STATEMENT OF GOVERNMENT SUPPORT

This invention was made with government support under contract #2015-10479 awarded by the National Institute of Food and Agriculture, U.S. Department of Agriculture. The government has certain rights in the invention.

BACKGROUND OF THE INVENTION

Field of Invention

The current disclosure provides for peptide-conjugated phosphorodiamidate morpholino oligomers (PPMOs) antisense oligonucleotides that target plant pathogens and insect pests. Methods of delivering PPMOs to bacteria in plants, in insect carriers, and to the insects via plant feeding are also provided.

Background

Antisense phosphorodiamidate morpholino oligomers (PMOs) downregulate target gene expression by interfering with the binding of ribosome to mRNA and thereby inhibiting protein translation (Iversen, P., Curr. Opin. Mol. Ther., (2001) 3:235-8). The PMO backbone is made of morpholino rings with phosphorodiamidate linkage, which protects them from nuclease degradation while still maintaining the complementary base pairing. Covalent conjugation of the PMO with membrane-penetrating peptides—resulting in protein-conjugated PMOs (PPMOs)—can enhance their cellular uptake by mammalian cells (Moulton et al, Bioconjug. Chem., (2004) 15:290-9) as well as bacteria (Tilley et al, Antimicrob. Agents Chemother., (2006) 50:2789-96).

Antisense oligonucleotides (ASOs), such as PPMOs, are short synthetic oligonucleotides that inhibit or modulate expression of a specific gene by Watson-Crick binding to cellular RNA targets. ASOs act through several different mechanisms and have a wide variety of structures and names. The present disclosure focuses on PPMOs in particular, and the structure and function of these molecules have been previously described (Moulton and Yan, Curr. Prot. Mol. Biol., (2008) 83: 26.8.1-26.8.29). Briefly, PMOs form stable base pairs with complementary nucleic acid sequences, but apparently do not bind to proteins to a significant extent. They are not recognized by proteins and do not undergo protein-mediated catalysis; nor do they mediate RNA cleavage by RNase H or the RISC complex (Abes et al, Biochem. Soc. Trans., (2007) 35:775-9; Daly et al, Meth. Mol. Biol., (2017) 1565:115-22). PMOs are typically used to inhibit translation of mRNA, splicing of pre-mRNA, and maturation of miRNA, although they can also inhibit other interactions between biological macromolecules and RNA ("Morpholino Oligomers. Methods in Molecular Biology", Moulton H., Moulton J. (eds). Vol. 1565. 2017. Humana Press, New York; Summerton, J., Biochim. Biphys. Acta, (1999) 1489:141-58).

Plant pathogens, especially bacteria are extremely difficult to target. Few antibiotics are approved for crops and current attitudes towards the risk of antibiotic resistance development have prevented the expansion of antibiotics into crops to reduce bacterial pathogens. As such, the need exists to develop non-antibiotic compositions and methodologies to target such pathogens.

Emerging severe bacterial plant pathogens cause hundreds of millions of dollars of damage to crops annually. One such pathogen, *Candidatus Liberibacter asiaticus* (CLas) in citrus, is spread in the U.S. by the Asian Citrus Psyllid, *Diaphorina citri* (Hemiptera: Liviidae). *Candidatus Liberibacter asiaticus*, CLas, bacterial infections result in citrus tree decline, lost yields, and tree death which threatens citrus production worldwide (de Graca and Korsten, Dis. Fruit. Veg., (2004) 1:229-45; Bove, J., J. Plant Pathol. (2006) 88:7-37; Canales et al., PLoS ONE (2016) 11:e0146223). A closely related pathogen, *Candidatus Liberibacter solanacearum* (CLso) in Solanaceous crops, like potato and tomato, causes Zebra Chip disease (ZC) in potatoes (Hansen et al., Appl. Environ. Micro. (2008) 74:5862-5; Liefting et al., Plant Dis. (2008) 92:1474; Liefting et al., Plant Dis. (2009) 93:208-14) which has caused millions of dollars in losses in the U.S. The insect vector is the tomato/potato psyllid, *Bactericera cockerelli* (Sůlc) (Hemiptera: Triozidae) (Munyaneza, Am. J. Pot. Res., (2012) 89:329-50).

Strains of *Xylella fastidiosa*, Xf, which are transmitted by many species of leafhoppers in the family Cicadellidae (Hemiptera) (e.g., the glassy-winged sharpshooter and blue-green sharpshooter), are associated with 'scorch-like" plant diseases, in fruit crops, grapevines, nuts, citrus, pears, peaches, and olives. In citrus a strain of Xf causes citrus variegated chlorosis (CVC), and has been linked to a sudden death pathotype. These strains of Xf can infect any type of citrus species, including hybrids. The severity of symptoms varies according to the genotype of the host with sweet oranges being the most susceptible, while grapefruit, lemons, limes mandarins, and trifoliates are only moderately susceptible (Garcia et al., Plant Dis. (2012) 96:1245-49; Gmitter et al., Tree Genet. Genomes (2012) 8:611-26; Casais et al., Pesquisa Agropecuaria Brasileira, (2014) 49:26-33; Fadel et al., Crop Protect. (2014) 64:115-21; Azevedo et al, Genetics Mol. Biol., (2016) 39:476-91). While CVC is not lethal in most cases, the infected trees always display reduced vigor, yield, and growth. Thus, infected trees have decreased productivity and lifespan (Garcia et al., supra).

While traditional treatment strategies (e.g., antibiotics) are being developed to address these concerns, there have been increasing problems associated with cost, registration, and public perception. Products which can target internal pathogens of plants and bacteria harbored internally in insect pests, could provide safer, highly specific treatments. Plants also depend upon their microbiota fauna to be healthy, thus treatments that may kill or reduce pathogens also needs to be safe for the beneficial host's microbes (Arora et al, BMC Biotechnol. (2015) 15:59). Herein, we provide RNA-targeting compositions and methodologies to meet these needs.

SUMMARY OF THE INVENTION

One embodiment provided by the disclosure herein is an oligonucleotide comprising at least one phosphorodiamidate morpholino residue, the oligonucleotide having a sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, and SEQ ID NO:49. In some embodiments, each residue of the oligonucleotide comprises a phosphorodiamidate morpholino residue. Such oligonucleotides can further comprise a peptide conjugated to the oligonucleotide.

Further provided herein is a method of inducing RNA silencing in a bacterium present in a plant-chewing or phloem-feeding insect comprising the step of: providing an oligonucleotide comprising at least one phosphorodiamidate morpholino residue to the insect in a manner whereby the insect to ingests the oligonucleotide, thereby contacting the bacterium with the oligonucleotide and thereby inducing RNA silencing. In some embodiments of this method, the insect ingests the oligonucleotide by consuming plant material containing the oligonucleotide. In some embodiments of this method, the plant material comprises leaf tissue, root tissue, stem tissue, flower tissue, phloem, or a combination of these. In particular embodiments, the insect is *Diaphorina citri* or *Diaprepes abbreviatus*. In some embodiments, the plant is a citrus plant (such as orange, lemon, clementine, lime, grapefruit, pomelo, citron, mandarin, and tangelo), an okra plant or a potato plant. In some embodiments, the method has the additional step of applying the oligonucleotide to a plant, such as by root soak, injection or foliar spray. In some embodiments, the method has the additional step of applying the oligonucleotide to an artificial diet, sugar solution or bait material.

The present disclosure also provides a method of controlling a plant-chewing or phloem-feeding insect, comprising the step of: providing an oligonucleotide comprising at least one phosphorodiamidate morpholino residue in a manner whereby the insect to ingests the oligonucleotide, thereby inducing RNA silencing and a detrimental effect to the insect. In some embodiments, the detrimental effect is increased mortality compared to insects not exposed to the oligonucleotide. In some embodiments, the insect is *Diaphorina citri* or *Diaprepes abbreviatus*. In some embodiments, the plant is a citrus plant. In some embodiments, the oligonucleotide is applied to a plant, such as by root soak, injection or foliar spray. In other embodiments, the oligonucleotide is applied to an artificial diet, sugar solution or bait material.

Further provided herein is a method of controlling bacteria present in an insect, comprising the steps of: 1) contacting a food source edible by the insect with an oligonucleotide comprising at least one phosphorodiamidate morpholino residue; 2) allowing the insect to feed on the food source, thereby ingesting the oligonucleotide; and 3) inducing RNA silencing in at least some of the bacteria present in the insect, thereby controlling the bacteria. In some embodiments, each residue of the oligonucleotide comprises a phosphorodiamidate morpholino residue. In particular embodiments, the oligonucleotide is any of the specific sequences described herein. In specific embodiments, the bacterium is *Candidatus Liberibacter asiaticus* or *Candidatus Liberibacter solanacearum*. In some embodiments, the food source is a plant, a bait material, an artificial diet, or a sugar solution. In still other embodiments, the food source is a plant and the oligonucleotide is contacted with the plant by root soak, injection or foliar spray. The food source can be a citrus plant. In particular embodiments, the insect is *Diaphorina citri* or *Diaprepes abbreviatus*.

Also provided in the present disclosure is a method of controlling a bacterium, wherein the bacterium is a plant pathogen present in plant tissues, comprising the steps of: 1) contacting the plant with an oligonucleotide comprising at least one with an oligonucleotide comprising at least one phosphorodiamidate morpholino residue in a manner whereby the oligonucleotide distributes through at least some of the plant tissues, thereby providing the oligonucleotide to the bacterium; and 2) contacting the oligonucleotide with the bacterium, thereby inducing a detrimental effect to the bacterium. In particular embodiments, the oligonucleotide has the sequence defined by SEQ ID NO:2, SEQ ID NO:5, SEQ ID NO:6, SEQ ID NO:8, SEQ ID NO:9, SEQ ID NO:10, SEQ ID NO:11, SEQ ID NO:12, SEQ ID NO:23, SEQ ID NO:24, SEQ ID NO:25, SEQ ID NO:26, SEQ ID NO:41, SEQ ID NO:42, SEQ ID NO:43, SEQ ID NO:44, SEQ ID NO:46, SEQ ID NO:47, SEQ ID NO:48, and SEQ ID NO:49. In specific embodiments, the bacterium is *Candidatus Liberibacter asiaticus* or *Candidatus Liberibacter solanacearum*. In some embodiments, the oligonucleotide is contacted with the plant by root soak, injection or foliar spray. In some embodiments, the plant is citrus or potato.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The patent application file contains at least one drawing executed in color. Copies of this patent or patent application publication with color drawing(s) will be provided by the Office upon request and payment of the necessary fee.

The novel features of the invention are set forth with particularity in the claims. Features and advantages of the present invention are referred to in the following detailed description, and the accompanying drawings of which:

FIG. 2A: 5% surfactant+PPMO. FIG. 2B: 1% surfactant+PPMO Leaf; FIG. 2C: PPMO and no surfactant.

FIG. 3A: Expression of wDi gyrA gene after incubating S2-wDi cells with PPMOs for seven days. The markers represent the expression of the target gene on the experimental condition compared to its expression on the untreated condition; values lower than 1.00 indicate gene suppression. Markers are means of triplicate experiments±SE. *P≤0.05; P≤0.01. FIG. 3B Density of viable wDi cells after being treated with PPMOs. Dead wDi correspond to bacterial cells incubated at 95° C. for 10 min. Bars are means of triplicate experiments±SE. Asterisk indicate significant reduction in wDi viability compared to control. *P≤0.001.

FIG. 4A provides graphic representation of transcript level of CLas gyrA gene after feeding infected adult psyllids with PPMOs for seven days. The markers represent the expression level of the bacterial gene on the experimental condition compared to its expression on the untreated condition; gene suppression is indicated by values lower than 1.00. Markers are means of triplicate experiments±SE. *P≤0.05. FIG. 4B provides graphic representation of CLas density after feeding infected adult psyllids with PPMOs for seven days. Bars are means of triplicate experiments±SE. *P≤0.05; ns: no significance.

FIGS. 6A and 6B. FIG. 6A provides a photomicrograph showing larval mid-gut tissue at 15 weeks (105 days) post feeding access to control diet (citrus plant with no PPMO). FIG. 6B provides a photomicrograph showing larval mid-gut tissue at 15 weeks (105 days) post feeding access to PPMO-containing citrus plant diet. Blue color indicates strong signal from propidium iodine nuclear staining. Yellow arrows mark signal associated to signal from lissamine labeled PPMOs.

Figure 1:
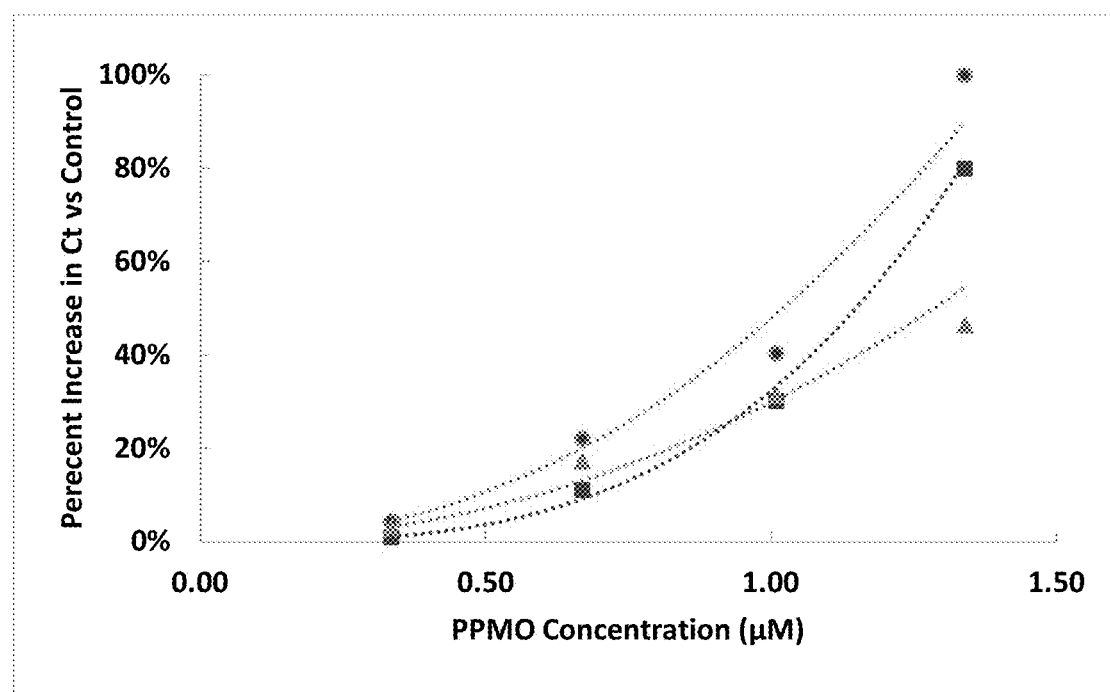
FIG. 1 provides an image of zPCR analyses of extracted psyllid homogenates spiked with increasing concentrations of PPMO. Displayed is the increase in Ct value mean with the addition of increasing PPMO concentrations. Increased binding of PPMO to the target transcript (gyr A), reduces available binding targets and increases Ct values. Quantitative qPCR analyses showing Ct values detecting gyrA CLas (square), *Wolbachia* (circle), and *Profftella* (triangle) across a concentration gradient post spiking treatment with PPMO. Values of Ct converted to percentage show that increasing concentration of PPMO in solutions results in increased suppression for each target.
Figure 2A:
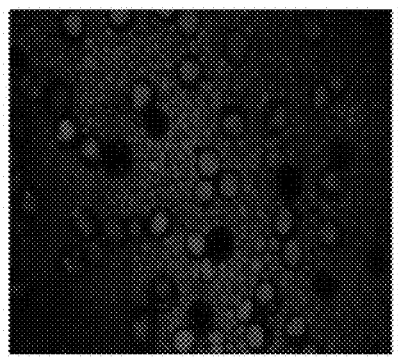
FIGS. 2A, 2B, and 2C provide confocal microscopic images showing delivery and detection of fluorophore-labeled PPMO in treated citrus leaves is increased with the use of surfactant.
Figure 2B:
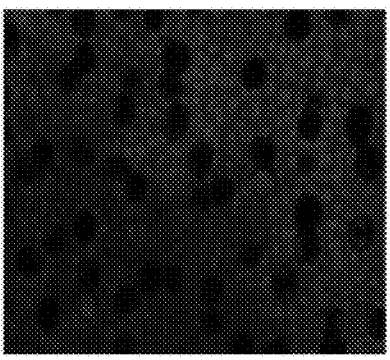
Figure 2C:

FIG. 9 provides a graphic representation of the effects of PPMOs on CLas titer in citrus plants. Treatment effect was expressed as percentage change in CLas titer [(mean titer after treatment—mean titer prior to treatment)/mean titer prior to treatment]×100. Means and standard errors are represented by bars and whiskers, respectively. Bars followed by an asterisk indicates significant change (increase or decrease) in CLas copy number as compared to that before treatment. The bar groupings represent, left to right, 2 days, 7 days and 14 days post PPMO treatment. In each group the clear bar is the untreated control, the gray bar is streptomycin treatment, the dashed bar is PPMO 1 (SEQ ID NO:2), and the checkered bar is PPMO 2 (SEQ ID NO:6).

FIG. 10 provides graphic representation of the effect of PPMOs on plant health in CLso-infected potato plants. Analyses at 7 weeks post PPMO treatments targeting Lso_gyrase A (SEQ ID NO:8) showed significant reduction in Symptom Severity in potato (PPMO treated~1.9 score, while CLso-infected was 3.0 highest severity score. Severity of foliar symptoms ranged from no symptoms (0) to severe symptoms (3). Error bars denote standard errors.

FIG. 11 provides graphic representation of the effect of PPMOs acquired from PPMO-containing potato plants on CLso titer in potato psyllids. Three psyllids were processed from each caged plant, for 5 groups (15 psyllids total per treatment). The psyllids feeding from PPMO (SEQ ID NO:8) treated potato plants had significantly lower CLso titers compare to the CLso-infected control psyllids.

FIG. 12 provides graphic representation of the reduction of *Wolbachia* and CLas in psyllid adults after feeding on PPMO-treated citrus seedlings. Error bars represent standard deviation of three technical replicates.

DETAILED DESCRIPTION OF THE INVENTION

In agricultural food production, some antibiotics have been commonly used to prevent infections in animals and plants and chemicals are used insecticides, antimicrobials and herbicides. Long-term and widespread use of these traditional methods leads to several common concerns, including drug-resistant bacteria, undesirable effects on beneficial species, and environmental impact. An alternative presented herein is the use of phosphorodiamidate morpholino oligomers (PMOs) and protein-conjugated PMOs (PPMOs). PMOs/PPMOs are typically used to inhibit translation of mRNA, splicing of pre-mRNA, and maturation of miRNA, although they can also inhibit other interactions between biological macromolecules and RNA. PMOs/PPMOs are effective, specific, and lack non-antisense effects. They work in any cell that transcribes and translates RNA. PMOs/PPMOs are synthetic uncharged P-chiral analogs of nucleic acids. The use of PMOs/PPMOs provides several strategies to modulate RNA and protein production across both eukaryotes and prokaryotes and have the potential to increase the effectiveness of biological control agents in the field, because of their high specificity for genetic targets.

PMOs/PPMOs of the present disclosure are single-stranded deoxyribonucleotides complementary to a targeted mRNA. Hybridization of PMOs/PPMOs to the target mRNA occurs via Watson-Crick base pairing and can result in specific inhibition of gene expression. The exact mechanism of action can vary depending on the chemical make-up of the PMO/PPMO and location of hybridization, but typically results in reduced levels of translation of the target transcript (Crooke 2004).

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991. Standard reference literature teaching general methodologies and principles of fungal genetics useful for selected aspects of the invention include: Sherman et al. "Laboratory Course Manual Methods in Yeast Genetics", Cold Spring Harbor Laboratory, Cold Spring Harbor, N.Y., 1986 and Guthrie et al., "Guide to Yeast Genetics and Molecular Biology", Academic, New York, 1991.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted.

As used in the specification and claims, use of the singular "a", "an", and "the" include plural references unless the context clearly dictates otherwise.

The terms isolated, purified, or biologically pure as used herein, refer to material that is substantially or essentially free from components that normally accompany the referenced material in its native state.

The term "about" is defined as plus or minus ten percent of a recited value. For example, about 1.0 g means 0.9 g to 1.1 g and all values within that range, whether specifically stated or not.

The term "a nucleic acid consisting essentially of", and grammatical variations thereof, means nucleic acids that differ from a reference nucleic acid sequence by 20 or fewer nucleic acid residues and also perform the function of the reference nucleic acid sequence. Such variants include sequences which are shorter or longer than the reference nucleic acid sequence, have different residues at particular positions, or a combination thereof.

"Citrus" as used herein refers to any species of tree producing any variety of citrus fruit, such as oranges, tangerines, clementines, lemons, limes, and the like.

For the purpose of the invention, the "complement of a nucleotide sequence X" is the nucleotide sequence which would be capable of forming a double-stranded DNA or RNA molecule with the represented nucleotide sequence, and which can be derived from the represented nucleotide sequence by replacing the nucleotides by their complementary nucleotide according to Chargaff's rules (A< >T; G< >C; A< >U) and reading in the 5' to 3' direction, i.e., in opposite direction of the represented nucleotide sequence. In the context of the present disclosure, this term also includes synthetic analogs of DNA/RNA (e.g., PPMOs).

The term "control", and grammatical variants thereof, is utilized in several contexts herein. Within experiments, a "control" is a means by which experimental variables are tested to eliminate as a cause of observed results. With regards to diseases (e.g., citrus greening), the term "control" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment. With regards to organisms (e.g., insects, bacteria, etc.), the term "control" as used herein refers to any means for preventing infection or infestation, reducing the population of already infected areas, or elimination of population(s) whose "control" is desired. Indeed, "controlling" as used herein refers to any indicia of success in prevention, elimination, reduction, repulsion, or amelioration of a target population or a problem caused by the target population (e.g., insect pest, microbe, etc).

The term "effective amount" of a composition provided herein refers to the amount of the composition capable of performing the specified function for which an effective amount is expressed. The exact amount required can vary from composition to composition and from function to function, depending on recognized variables such as the compositions and processes involved. An effective amount can be delivered in one or more applications. Thus, it is not possible to specify an exact amount, however, an appropriate "effective amount" can be determined by the skilled artisan via routine experimentation.

"Insect" or "insect pest" as used herein means any variety of insects that may cause harm to plants, trees, fruits, or nuts or products produced thereby or therefrom. In exemplary embodiments, such pests include leaf-eating and sap-feeding arthropods, such as the Asian citrus psyllid.

The term "plant" includes whole plants, plant organs, progeny of whole plants or plant organs, embryos, somatic embryos, embryo-like structures, protocorms, protocorm-like bodies (PLBs), and suspensions of plant cells. Plant organs comprise, e.g., shoot vegetative organs/structures (e.g., leaves, stems and tubers), roots, flowers and floral organs/structures (e.g., bracts, sepals, petals, stamens, carpels, anthers and ovules), seeds (including embryo, endosperm, and seed coat) and fruit (the mature ovary), plant tissue (e.g., vascular tissue, ground tissue, and the like) and cells (e.g., guard cells, egg cells, trichomes and the like). Any plant on which *P. penetrans* nematodes feed are included in this invention.

As used herein, "preventing" a disease refers to inhibiting the full development of a disease.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch, J Mol Biol, (1970) 48:3, 443-53). A computer-assisted sequence alignment can be conveniently performed using a standard software program such as GAP which is part of the Wisconsin Package Version 10.1 (Genetics Computer Group, Madison, Wis., USA) using the default scoring matrix with a gap creation penalty of 50 and a gap extension penalty of 3.

PMO/PPMO Compositions

PMOs and PPMOs chemistries are known and, for the purposes of the disclosure herein, the method of making them can be varied to encompass any construction methodology, such as that disclosed in Wesolowski et al., PNAS (2011) 108:16582-87 and Wesolowski, Alonso and Altman, PNAS (2013) 110:8686-9), both of which are specifically incorporated here by reference. Generally speaking, PPMOs of the present invention are between 14-18 nucleotides when targeting bacterial genes. Preferably, PPMOs do not have more than three consecutive guanine residues, and preferably have between 35-65% GC content. Preferred PPMOs of the present disclosure have 100% match to the target RNA sequence, however, PPMOs with 1, 2, or 3 base pairs not matching the target sequence are also contemplated.

TABLE 1

| PPMO sequences | |
|---|---|
| Gene Target | SEQ ID NO: |
| E. coli gyr-A-1; | SEQ ID NO: 1 |
| E. coli gyr-A-2; | SEQ ID NO: 2 |

TABLE 1-continued

PPMO sequences

| Gene Target | SEQ ID NO: |
|---|---|
| clgyrA-14; wolb-ds gyrA; PDS | SEQ ID NO: 3 |
| PWGYRA-14 | SEQ ID NO: 4 |
| Xyl gyrase A | SEQ ID NO: 5 |
| CLas-gyrase-A tagged | SEQ ID NO: 6 |
| Wolb-Dc gyrase-A | SEQ ID NO: 7 |
| LSO-GyrA 1 | SEQ ID NO: 8 |
| La-GyraseA 1 | SEQ ID NO: 9 |
| La-GyraseA 2 | SEQ ID NO: 10 |
| La-GyraseA 3 | SEQ ID NO: 11 |
| La-GyraseA 4 | SEQ ID NO: 12 |
| Wol-GyraseA 1 | SEQ ID NO: 13 |
| Wol-GyraseA 2 | SEQ ID NO: 14 |
| Wol-GyraseA 3 | SEQ ID NO: 15 |
| Wol-GyraseA 4 | SEQ ID NO: 16 |
| Pa-GyraseA 1 | SEQ ID NO: 17 |
| Pa-GyraseA 2 | SEQ ID NO: 18 |
| Pa-GyraseA 3 | SEQ ID NO: 19 |
| Pa-GyraseA 4 | SEQ ID NO: 20 |
| BC-GyrA-1 | SEQ ID NO: 21 |
| BC-GyrA-2 | SEQ ID NO: 22 |
| La-Rib 1 | SEQ ID NO: 23 |
| La-Rib 2 | SEQ ID NO: 24 |
| La-Rib 3 | SEQ ID NO: 25 |
| La-Rib 4 | SEQ ID NO: 26 |
| Pa-Rib 1 | SEQ ID NO: 27 |
| Pa-Rib 2 | SEQ ID NO: 28 |
| Pa-Rib 3 | SEQ ID NO: 29 |
| Pa-Rib 4 | SEQ ID NO: 30 |
| Cr-DNB 1 | SEQ ID NO: 31 |
| Cr-DNB 2 | SEQ ID NO: 32 |
| Cr-GrL 1 | SEQ ID NO: 33 |
| Cr-GrL 2 | SEQ ID NO: 34 |
| Cr-GrL 3 | SEQ ID NO: 35 |
| Cr-GrL 4 | SEQ ID NO: 36 |
| Pa-Ligase 1 | SEQ ID NO: 37 |
| Pa-Ligase 2 | SEQ ID NO: 38 |
| Pa-Ligase 3 | SEQ ID NO: 39 |
| Pa-Ligase 4 | SEQ ID NO: 40 |
| La-Ligase 1 | SEQ ID NO: 41 |
| La-Ligase 2 | SEQ ID NO: 42 |
| La-Ligase 3 | SEQ ID NO: 43 |
| La-Ligase 4 | SEQ ID NO: 44 |
| Wol-Hv-gyraseA-1 | SEQ ID NO: 45 |
| Xyl-Ligase 1 | SEQ ID NO: 46 |
| Xyl-Ligase 2 | SEQ ID NO: 47 |
| Xyl-Ligase 3 | SEQ ID NO: 48 |
| Xyl-Ligase 4 | SEQ ID NO: 49 |

TABLE 2

Genomic sequences of target genes

| Gene | SEQ ID NO: |
|---|---|
| CLas DNA gyrase A | SEQ ID NO: 50 |
| CLas NAD-dependent DNA ligase A | SEQ ID NO: 51 |
| CLas Methionine-tRNA ligase | SEQ ID NO: 52 |
| CLas peptide deformylase | SEQ ID NO: 53 |
| CLas CTP synthase | SEQ ID NO: 54 |
| CLas GlmU | SEQ ID NO: 55 |
| *Diaphorina citri* strain LSPolk2000 wingless (wg) gene | SEQ ID NO: 56 |
| *Xylella fastidiosa* Gyrase A | SEQ ID NO: 57 |
| Wolb-Dc Gyrase A | SEQ ID NO: 58 |
| CLso Gyrase A | SEQ ID NO: 59 |
| *Baumannia cicadellinicola* GyrA | SEQ ID NO: 60 |
| *Escherichia coli* GyrA subunit A | SEQ ID NO: 61 |

In particular embodiments, the present invention provides a composition having an inhibitory PPMO having a sequence provided in Table 1. Typically, PPMOs of the present invention are provided to a target recipient (e.g., plant, insect or bacteria) in an amount sufficient to inhibit production of the polypeptide encoded by one or more of the full-length genes targeted by the PPMO. In particular embodiments, the gene target is one or more of the genes provided in Table 2.

For example, a PMO/PPMO of the present invention is applied to a plant topically, allowing for uptake by the plant. The PPMO can control a bacterial pathogen currently infecting the plant. Following uptake by the plant, the PMO/PPMO contacts bacteria internal to the plant. PMOs/PPMOs located internally to a plant or topically thereon can be ingested by an insect, thus contacting the insect. Additionally, when a plant pest (e.g., *D. citri*) is feeding on a treated plant, the insect can ingest a sufficient level of the PMO/PPMO to control or kill bacteria harbored by the insect pest and/or control or kill the insect pest itself.

In addition to a PMO/PPMO of the present invention, compositions of the present invention intended to be applied to a plant can be formulated to contain one or more phagostimulants, pesticides, fungicides, or combinations thereof. The composition can be formulated to be coated on a plant, plant part, plant tissue (e.g., root or leaf), or seed. In certain aspects the PMO/PPMO is combined with one or more excipients, buffering agents, carriers, etc. Such components are well known in the art and readily chosen for various applications by one skilled in the art.

Typically, a PMO/PPMO of the present invention is provided to a target insect pest, target plant in need of treatment, or target microbe in an amount sufficient to inhibit production of the polypeptide encoded by one or more of the full-length genes targeted by PMO/PPMO. For example, when an insect pest is feeding on PPMO-laden plant material (e.g., leaf), the insect ingests a sufficient level of PPMO to result in a phenotypic effect on bacteria harbored in its gut. In some embodiments, a combination of two or more PPMOs can be combined in a single plant. In embodiments where two or more PPMOs are combined in a single plant, the PPMOs can target different genes or different portions of the same gene from the same or different targets. Thus, in one embodiment, a single plant material can be used to deliver multiple, different PPMOs targeting the production of one or more proteins made by the treated plant, the insect pest, and/or a microbe present in the plant or in the insect. Where two or more PPMOs are taken up and distributed throughout the plant material, the PPMOs can be provided to the plant in a single solution, or in multiple, sequentially-applied solutions.

In addition to PPMOs, compositions of the present invention that are intended to be applied to a plant can also comprise one or more chemoattractants, phagostimulants, visual attractants, insecticides, pheromones, fungicides, or combinations thereof. Such additional components are well known in the art and are readily chosen to complement compositions of the present invention, but are not specifically integral to the present invention. These additional components can be formulated to be coated on a plant, plant part, leaf, fruit, vegetable, stem or other plant structure. In certain aspects the additional component(s) are combined with one or more excipients, buffering agents, carriers, etc. that are also well known in the art.

Where additional components are applied in a coating, the coating can be formulated as a spray or dip so that the additional non-PPMO components remain on the exterior of the plant material. For example, a leaf having a PPMO distributed through at least part of its vascular system can be coated with a composition comprising one or more chemoattractants, phagostimulants, visual attractants, insecticides, pheromones, fungicides, or combinations thereof. Alternately, the additional component can be mixed with an aqueous solution containing the PPMO(s) to be taken up and distributed via vascular action of the plant material, or osmosis through the plant material, thus distributing the PPMO(s) and the additional component(s) throughout at least part of the plant material.

Application to Target Plants

Compositions of the invention disclosed herein can be applied to soil, fruits, vegetables, crops, and any other desired target using any delivery methodology known to those of skill in the art. For example, PPMO-containing compositions can be applied to the desired locale via methods and forms including, but not limited to, shank injection, sprays, granules, flood/furrow methods, sprinklers, fumigation, root soaking and drip irrigation. In embodiments of the invention where the compositions are sprayed onto a desired locale, the compositions can be delivered as a liquid suspension, emulsion, micro-emulsion or powder. In other embodiments, granules or microcapsules can be used to deliver the compositions of the invention.

The compositions of the present invention can be applied to plants and/or crops by any convenient method, for example, by using a fixed application system such as a center pivot irrigation system. Preferably, application to fields of plants and/or crops is made by air spraying, i.e., from an airplane or helicopter, or by land spraying. For example, land spraying can be carried out by using a high flotation applicator equipped with a boom, by a back-pack sprayer or by nurse trucks or tanks. Compositions (PPMOs) can also be added to baits, feeds, liquids, solutions, mixtures or compositions designed to be ingested by a target insect. One of skill in the art will recognize that these application methodologies are provided by way of example and that any applicable methods known in the art or developed in the future can be utilized.

Having generally described this invention, the same will be better understood by reference to certain specific examples, which are included herein to further illustrate the invention and are not intended to limit the scope of the invention as defined by the claims.

EXAMPLES

Example 1

Production of PPMO Molecules

PPMOs were prepared for each of the oligonucleotides listed in Table 1. The gene sequences were selected from the microbial database when targeting microbes, and NCBI, nr database and NAL psyllid genome database, for the psyllid targets. PPMOs were designed utilizing software from Gene Tools, LLC., to meet the following general requirements: 1) less than 40% GC content; 2) no more than three consecutive guanine residues, and 3) an overall length of between 15 nt and 18 nt. Conjugation of the cell-peptide protein, PP, was performed by Oregon State University, Service Lab, Corvallis, Oreg. The PPMOs were synthesized by Gene Tools, LLC (Philomath, Oreg.) using a method previously described (Wesolowski et al., PNAS (2011) 108:16582-87; Wesolowski, Alonso and Altman, PNAS (2013) 110:8686-9).

The external guide sequence (EGS) of some PPMOs were designed to be complementary to a conserved region of the DNA gyrase A gene (gyrA) found in most bacteria (SEQ ID NO:1, SEQ ID NO: 2, SEQ ID NO:3, SEQ ID NO:5, SEQ ID NO:6, SEQ ID NO:7, SEQ ID NO:8, SEQ ID NO:21, and SEQ ID NO:22). The original control positive was 100% perfect reverse complement to CLas gyrA target sequence in *E. coli* (SEQ ID NO: 2, SEQ ID NO:3, SEQ ID NO:5, SEQ ID NO:6, SEQ ID NO:7) (Wesolowski et al, (2013) supra). This sequence is predicted to bind with various degrees of affinity based upon the number of mismatches, or single nucleotide polymorphisms, SNP's.

Example 2

PPMO Primer Binding Method for Activity Efficiency

Binding efficiency of PPMO's have been shown to be reduced with the increase in the number of single nucleotide polymorphisms (SNPs) in the target sequence (Wesolowski et al, (2011) supra; Wesolowski et al, (2013) supra). The external guide sequence (EGS) of the PPMOs were designed to be complementary to a conserved region of the DNA gyrase A gene (gyrA) found in most bacteria (SEQ ID NO:1, SEQ ID NO: 2, SEQ ID NO:3, SEQ ID NO:5, SEQ ID NO:6, SEQ ID NO:7, SEQ ID NO:8, SEQ ID NO:21, SEQ ID NO:22, and SEQ ID NO:45).

*Candidatus Profftella armature, Wolbachia* wDi, *Candidatus Liberibacter asiaticus.*

The target binding efficiency of this specific PPMO construct was tested using PPMO primer binding methods. Primers were designed to flank or overlap each of the three bacterial target sequences. Using total DNA extracted from psyllid colonized by each bacterium, primers pairs were then validated using standard PCR and gel electrophoresis. As expected based on previously reported results (Moulton and Yan, 2008), a 100% match between the PPMO and target sequence resulted in 100% binding affinity, while less than a 100% sequence match decreased binding efficiency (data not shown).

Extracted Psyllid samples were spiked with increasing concentrations of PPMO then run on qPCR using the previously validated primers. Increased binding of PPMO to the target means less available target. In the host, it is expected that PPMO binding equates with RNA knockdown and a corresponding effect (e.g., death). Results from quantitative qPCR analyses showing Ct values detecting CLas (square), *Wolbachia* (circle), and *Profftella* (triangle) across a concentration gradient post treatment with PPMO are provided in FIG. 1. Values show that increasing concentration of PPMO added to samples resulted in increasing mean Ct values for each target. Thus, the more binding, the greater the predicted effect.

Example 3

Delivery of PPMO to Plant Tissues

Topical Foliar Spray Assay (Entire Canopy).

A solution of 1 mL volume containing 20.14 nmol of fluorescently-labeled PPMO (SEQ ID NO:2) was added to a 10 mL glass vial. Then 5 mL of Milli-Q, filtered water was added to the vial and vortexed 30 seconds to mix. The PPMO solution was then mixed with either a 1% or 5% surfactant Silwet® L-77 (Momentive, 14610 W. 106th Street, Lenexa, Kans., 66215, USA).

The PPMO solution was diluted in the surfactant to a final concentration of 1% by adding 1 mL of the stock-2 dilution into a 10 mL glass vial. Next, 1.2 mL of 5% surfactant and 3.8 mL clean water were mixed by vortexing prior to the spraying step. To prepare a PPMO solution at a final concentration of 5% surfactant, 1 mL of the stock-2 dilution was added into a 10 mL glass vial. Next, add 3.0 mL of 10% chemical and 2.0 mL clean water were added and mixed by vortexing prior to the spraying step. The pot or cone with the plant was placed in a plastic bag using a zip tie to seal it at the base of the trunk. The entire canopy was sprayed with the selected treatment. After the solution dried, the bag was removed. Treated leaves were misted with water 1-hour post treatment. When watering, water was added directly to the soil. Leaves were lightly spritzed with water 2× per week to reconstitute the PPMO solution, taking care not to drip onto the roots.

Untreated leaves at the top of tree branches, and root samples from both the control and PPMO treated trees were collected five (5) days post application. Sections of fresh plant tissue, midrib, and tips of leaf were cut longitudinally and in cross section for analysis. Leaf pieces were mounted directly onto slides in Fluoromount™, topped with a coverslip, and sealed. Imaging of the tissue slide preparations was performed within 48 hrs using a confocal microscope. Scan depths were between 5 and 10 microns at a time through tissues, from the dorsal to the ventral surface, permitting images to be stacked by computer imaging software program.

In initial trials, leaves showed probe only on surface in initial trials due to rapid drying, preventing significant absorption. To increase absorption, the addition of a surfactant was tested. Samples containing the surfactant provided significant improved absorption into citrus leaves at both concentrations tested (FIGS. 2A, 2B, and 2C). The surfactant is presumed to enlarge leaf stomata, which increases water (and therefore PPMO solution) absorption.

Citrus Cutting Assay.

Citrus cuttings were obtained and prepared using methods specified previously (Andrade & Hunter, Entomol. Exper. Applic., (2017) 162:389-96). A solution of 20.14 nmoles of fluorescently-labeled PPMO (SEQ ID NO:6) was absorbed into the cuttings. The solution was almost completely absorbed after 24 hrs. Plant material was collected by cutting above the vial top to prevent chance of contamination from treatment solution. The cuttings were then washed and placed on a slide with a mixture of Fluoromount™ and PBS buffer.

Results were determined by confocal microscopy of leaf and petiole tissues and microplate spectrophotometry and showed that PPMOs were systemically delivered to plant tissues. Clearing methods were used to reduce autofluorescence in plant tissues due to chloroplasts. Confocal microscopy of leaves from PPMO treated cuttings had significantly more signal than leaves and petioles sampled from the control cuttings. Deep scan of cleared leaf tissue revealed systemic delivery of PPMO into cells (data not shown).

Root Absorption Assay.

Three citrus seedlings (varieties (Carrizo, Madam vinous, and Tangelo, cv. Sun Cha Citrus, designated *Citrus* X *tangelo* [J. Ingram & H. E. Moore] (*C. paradisi* X *C. reticulata*)) were chosen based on identical health, height and canopy. Seedlings were rinsed with water and removed from soil pots. Seedling roots were rinsed in cold tap water to remove soil. The root tips of one of the seedlings was excised approximately 2 in above the end of the roots. Three 1 L flasks were filled with 1 L of DI water. A fluorescently-labeled PPMO (SEQ ID NO:6) solution, 100 μL of 201.4 μM, was added to two of the flasks and mixed well. The roots of two of the seedlings were submerged into the PPMO solution, one with cut roots and one with roots uncut. The roots of the third seeding were submerged in 1 L of water only. The seedling absorbed approximately 100 mL of the solution.

Two leaves from each seedling were collected 7 d and 12 d post-treatment. Leaves were homogenized in liquid nitrogen using mortar and pestle. 2 mL of Mili-Q water was added to each mortar and mixed with the leaf tissue. 1 mL of liquid from each of the homogenized leaf samples was pipetted into 1.5 mL centrifuge tubes. 2 μL of Proteinase K was added to each sample and incubated for 30 mins at 55 C°. Samples were then incubated at room temperature for another 30 mins. Samples were centrifuged for 1 min at 10,000 g and the supernatant was loaded into the H1 Synergy Microplate reader. The excitation of the samples was fixed to 530 nm with emission start at 400 nm and emission stop at 640 nm with a step of 10 nm.

PPMOs were successfully delivered to the upper leaves of citrus seedlings using naked root immersion methods. Fluorescently labeled PPMOs were detected by microplate reader in leaf tissue collected from PPMO treated seedlings 12 d post treatment; however, PPMOs were not detected 7 d post treatment. Leaves sampled 12 d post-treatment from PPMO treated seedlings had significantly higher microplate readings in this region compared to leaves sampled from the water treated seedling. This suggests successful delivery of PPMOs to the upper leaves of citrus seedlings when roots are submerged in PPMO solution. No significant difference in microplate detection was observed in the roots with uncut versus cut root tips (data not shown).

Soil Drench Assay.

A 500 mL solution containing 265 nmoles of PPMO was prepared in a 1 L flask. Two small, potted *Murraya paniculata* seedlings were used for treatment. 100 mL of PPMO (SEQ ID NO:6) treatment solution was applied directly to the soil of one of the potted plants and 100 mL of DI water was applied to the other potted plant. This was repeated for five days. Two upper leaves of the potted *M. paniculata* seedlings were collected on the fifth day of treatment. Leaves were processed for the microplate reader as previously described. PPMOs were successfully delivered systemically to potted plants when applied as a soil drench. Upper leaves sampled from PPMO treated plants had significantly higher microplate readings in the 580 to 600 nm wavelength region compared to leaves sampled from the water treated *M. paniculata* (data not shown).

Topical Foliar Spray Movement Assay (Lower Canopy).

Two citrus seedlings in black Conetainers™, in good shape approximately 45 cm tall were selected. Treatments: water (control) and fluorescently-labeled PPMO (SEQ ID NO:6). Prior to spraying lower leaves, upper leaves were covered with plastic wrap or wax paper to prevent accidental spray contact. The base of the tree including the pot was also covered with wax paper, so as not to get treated.

Clay Particle Delivery Assay.

A 25 mL solution containing 20.14 nmoles of PPMO (SEQ ID NO:6) was prepared in a 50 mL tube. A weight of 35 grams of large Oil-Dri clay particles [(Oil-Dri, Corp, 410 N. Michigan Ave., Chicago, Ill. 60611) samples being representative of the clays known as "Montmorillonite"]. Clay pellets were weighed and slowly added to the 25 mL solution of PPMO. Two 1-gallon pots containing soil were obtained. One third of the soil from each pot was transferred to two 1 L beakers. Two small citrus seedlings were transplanted into the 1-gallon pots. After the PPMO solution was completely absorbed into the clay, the PPMO+clay was mixed into one of the containers of soil using a spatula. The PPMO+Clay treated soil was then used to fill in around the roots of one of the seedlings. The potted trees were placed underneath grow lights, on top of a plastic overflow tray, to collect water. 200 mL of was applied to the soil of each transplanted citrus tree. Plants were watered every Monday and Friday, using 200 mL of water.

Microplate Reader Analyses.

First sample (day 0) collection: 1 or 2 leaves as needed were collected from the lowest leaves on plants for both the control and PPMO treated trees. Subsequent collections (at various time-points post treatment—including 5 days, 15-17 days, 30-35 days, 60-65 days, and 90-95 days) were of leaves at the third or fourth node down from the most apical tip of the tree. Analyses used a H1 Synergy Microplate Reader. Samples homogenized in equal volumes of water, gently centrifuged for 30 sec to pellet heavy debris, and 100 uL of solution removed from top of each sample preparation.

Results.

Results from all delivery routes showed the presence of PPMOs in leaf tissues, indicating a wide variety of application methods will result in the presence of PPMOs in plant tissues and that the PPMOs move throughout the plant, regardless of site of application. PPMOs were detected in samples from 5 days post application to 95 days post application indicating the long-term stability of these molecules in planta (data not shown).

Example 4

In Vitro PPMO Efficacy Assays
Cell Cultures

S2 (*Drosophila* Schneider 2) cells were cultured using Schneider's *Drosophila* medium (Thermo Fisher Scientific, Waltham. Mass.) containing 10% fetal bovine serum (heat-inactivated FBS; Thermo Fisher Scientific) and 1% Penicillin-Streptomycin (50 units penicillin-50n streptomycin sulfate per milliliter of medium). The cells were kept in a non-humidified incubator at 28° C. and subcultured every three days to a final density of ~1×10$^6$ cell/mL. S2 cells infection with *D. citri* Wolbachia strain (wDi) was completed according to Bonilla et al., 2018.

*Diaphorina citri* Cultures

Psyllids harboring CLas were obtained from a colony reared on infected 'Pineapple' sweet orange plants (*Citrus sinensis* (L.) Osb), maintained in a quarantined facility at the University of Florida Citrus Research and Education Center (Lake Alfred, Fla.). The psyllid colony was maintained at 26±1° C., a 16:8 (L:D) hrs photoperiod and 60-80% relative humidity. Random insect and plant samples were tested monthly to confirm the presence of the bacterium, using a qPCR procedure described previously (Pelz-Stelinski et al, J. Econ. Entomol., (2010) 103:1531-41).

Cell Culture Assays

S2 cells infected with wDi were seeded at a density of 2.75×10$^5$ cells/mL. After 24 hrs the cells were incubated with a PPMO of SEQ ID NO:2 or of SEQ ID NO:4 at a 5 µM concentration. The insect cells were incubated with the PPMOs for seven days at 28° C. Each treatment (untreated, SEQ ID NO:2, and SEQ ID NO:4) was replicated three times.

*Wolbachia* (wDi) Viability Assay wDi cells (a *D. citri* endosymbiont) were extracted from S2 cells as described previously (Gamston & Rasgon, J. Vis. Exp., (2007) 5:e223, doi:10.3791/223). Briefly, the bacterial cells were lysed at room temperature with sterile 3 mm borosilicate glass beads, followed by centrifugation of the resultant supernatant at 2,500×g per 10 min at 4° C. A second centrifugation step (18,000×g per 10 min at 4° C.) was preceded by sieving the supernatant through a 5 µm sterile filter. The bacterial pellet was resuspended in Schneider's *Drosophila* medium and finally purified using a 2.7 µm filter.

Isolated wDi cells were seeded at a density of 300,000 cells/mL in 96-well culture dishes (Corning Incorporated, Corning, N.Y.) and incubated with the peptide-conjugated morpholinos at a 5 µM concentration. Four days post treatment, 800 µL of cell suspension was divided into two equivalent samples; one was kept untreated whereas the other was first mixed with 100 µL of PMA Enhancer for Gram Negative Bacteria (Biotium, Hayward, Calif.), followed by 5 µL of propidium monoazide 2.5 mM (PMAxx; Biotium). The samples were incubated in the dark, with constant shaking, for 10 min at room temperature and then exposed to intense visible light for 15 min (PMA-Lite; Biotium). After crosslinking the bacterial DNA with the propidium monoazide, the wDi cells were pelleted by centrifugation (5,000×g for 10 min) and their DNA extracted using the DNeasy Blood & Tissue Kit (QUIAGEN, Valencia, Calif.). An 800 µL wDi suspension was heat inactivated for 5 min at 95° C., processed as stated before and used as a dead control sample.

Bacterial copy number was quantified by using dilution series of a purified wDi gyrA gene fragment (250 bp), to generate a standard curve through qPCR reactions. Delta threshold cycles values (Ct of sample with PMA—Ct of sample without PMA) were used to obtain an estimate of alive wDi cells. QuantStudio 6 Flex Real-Time PCR Instrument (Thermo Fisher Scientific) and Syber Green PCR Master Mix (Thermos Fisher Scientific) were used for the qPCR reactions. The standard curve obtained for wDi was ($y=-3.594x+3.796$; $R^2=0.99$). wDi copy number was compared between the treatments by using One-way analysis of variance (ANOVA); the treatment groups mean were compared to the control group mean by Dunnett's test. A P-value equal or less to 0.05 was considered statistically significant. STATISTICA 13.3 (TIBCO Software) and GraphPad Prism (GraphPad Software, La Jolla Calif.) were used for the statistical analysis.

For gene expression analysis, total RNA was extracted from S2+wDi cells or *D. citri* adults using the Direct-Zol RNA MiniPrep (Zymo Research, Irvine, Calif.) according to the manufacturer instructions. RNA concentration and quality were analyzed by spectrophotometry (Nanodrop 2000;

Thermo Scientific). cDNA was synthesized from 1 μg of total RNA using the High Capacity cDNA Reverse Transcription kit (Thermo Fisher Scientific). Quantitative PCR assays were conducted using a QuantStudio 6 Flex Real-Time PCR Instrument (Thermo Fisher Scientific) and the Syber Green PCR Master Mix (Thermos Fisher Scientific). Relative expression of the wDi gyrA and CLas gyrA genes was calculated by the comparative critical threshold (AACt) method (Livak & Schmittgen, Methods (2001) 25:402-8), comparing the expression level of the target mRNA in PPMO-treated samples to its expression in untreated samples. The wDi gene wsp and the CLas outer membrane protein (omp) gene were used as internal controls for cell culture and insect bioassays, respectively. Primer3 v. 0.4.0 software (Untergrasser et al, Nucl. Acids Res. (2012) 40:e115) was used to design primer pairs for the target and the reference genes. PCR efficiencies of target and internal control genes were confirmed to be within the range of 90-110% for all qPCR assays.

PPMOs Reduced wDi gyrA mRNA Expression and Affected the Viability of wDi Cells

Figure 3A:
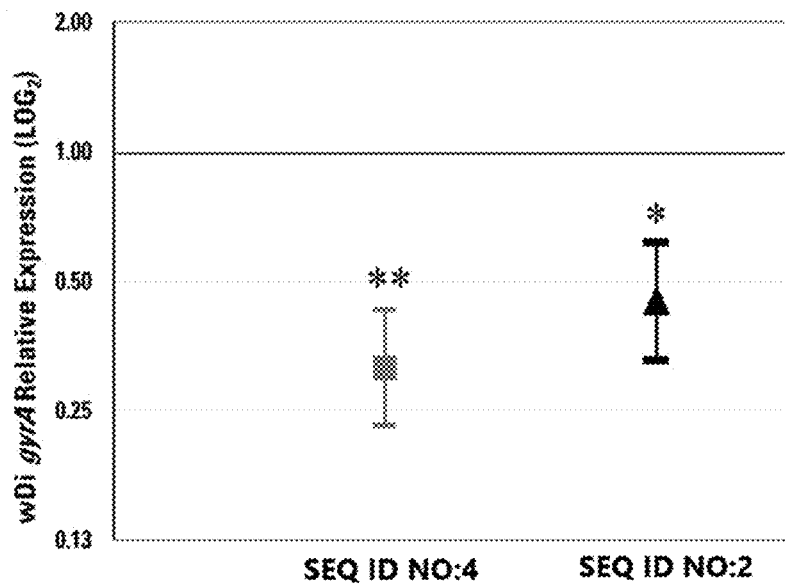
FIGS. 3A and 3B.

To test the capability of PPMOs to degrade bacterial mRNAs in cultured insect cells, *Drosophila* S2 cells infected with *Wolbachia* from *Diaphorina citri* (S2+wDi) were incubated with a 5 μM PPMO solution (SEQ ID NO:2 or SEQ ID NO:4) for seven days. Total RNA was extracted from the cells and analyzed by qRT-PCR using primers specific to wDi DNA gyrase A gene (wDi gyrA). The wDi gyrA transcript level was significantly reduced by 68% when S2-wDi cells were incubated with SEQ ID NO:2, compared to untreated cells (U=9.0, n1=n2=9, p=0.006). SEQ ID NO:4 reduced the expression of wDi gyrA by 55% when contrasted to its expression in non-treated cells (two sample K-S test, p<0.05) (FIG. 3A).

Figure 3B:
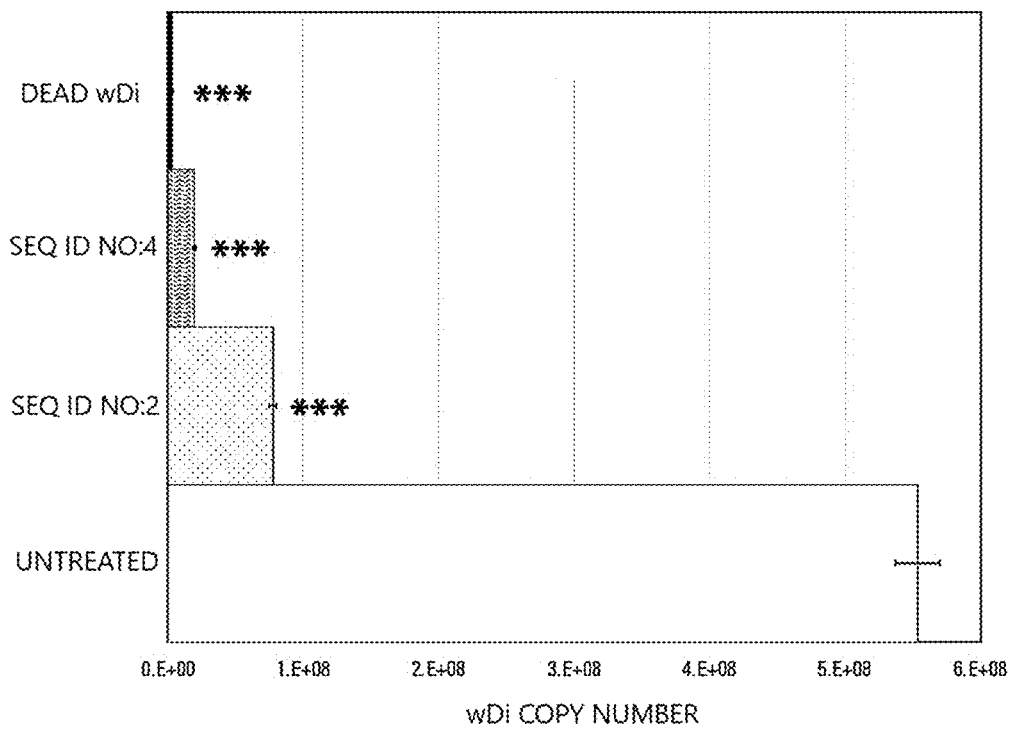

The effect of PPMOs on bacterial viability was evaluated by isolating wDi cells from S2 cells, followed by incubation with a PPMO (SEQ ID NO:2 or SEQ ID NO:4) 5 μM solution for four days. Before quantifying the bacterium copy number by qPCR, the cells were treated with propidium monoazide which allowed the detection of alive wDi by penetrating cells with compromised membranes (dead cells), covalently linking to the DNA and inhibiting PCR amplification (Nocker et al., 2007). There was a significant difference in the density of viable wDi between the treatments (F [3, 8]=997.1, p<0.0001). Compared to untreated *Wolbachia* cells, both PPMO treatments greatly reduced the number of viable wDi cells (FIG. 3B). The results suggested that the RNase P-mediated repression of the DNA gyrase subunit A gene is lethal for the *Wolbachia* cells.

Example 5

PPMO Delivery to Insects Via Feeding
In Silico Feeding.

PPMOs were delivered to *D. citri* adults using a feeding system consisting of a bottomless petri dish (35 mm×10 mm), two pieces of stretched Parafilm (American National Can) and a filter paper disc (Russell & Pelz-Stelinski, Entomol. Exp. Appl., (2015) 154:171-6). An artificial diet composed of 17% (w:v) sucrose in water, mixed with 0.5% green food dye (McCormick & Company, Baltimore, Md.), was applied on the filter paper between the Parafilm layers. PPMOs of SEQ ID NO:2 or SEQ ID NO:4 were diluted to 5 μM into the artificial diet. Sixteen teneral adult psyllids (eight males, eight females), infected with CLas, were placed in each petri dish and allowed to feed for seven days. Control samples consisted of infected psyllids exposed to only sucrose solution. Three replicates were conducted for each treatment. The feeding assays were held in an environmental incubator at 16:8 h light:dark cycle, 27±2° C., and 60-65% relative humidity.

Results.

Figure 4A:
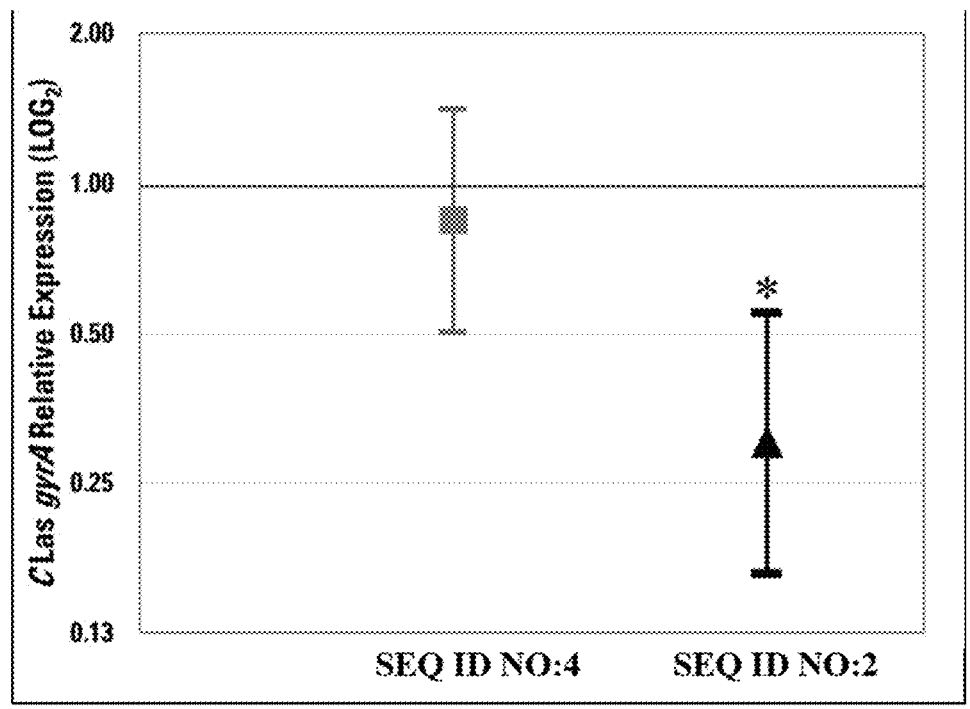
FIGS. 4A and 4B.

To examine the efficacy of PPMOs in silencing bacterial genes in vivo, *D. citri* adults were fed an artificial diet containing PPMOs of SEQ ID NO:2 or SEQ ID NO:4 at a 5 μM concentration. Seven days post-treatment, total RNA was extracted from the psyllids and analyzed by qRT-PCR, using primers specific to the CLas gyrA gene. A 70% repression of the CLas gyrA transcript was observed when adult psyllids where fed the artificial diet containing SEQ ID NO:2, compared to untreated psyllids (t (16)=−2.638, p=0.018). There was no significant difference in the amount of CLas gyrA mRNA, between psyllids that were fed PWgyrA-14 and untreated psyllids (t (16)=1.226, p=0.238) (FIG. 4A).

Figure 4B:
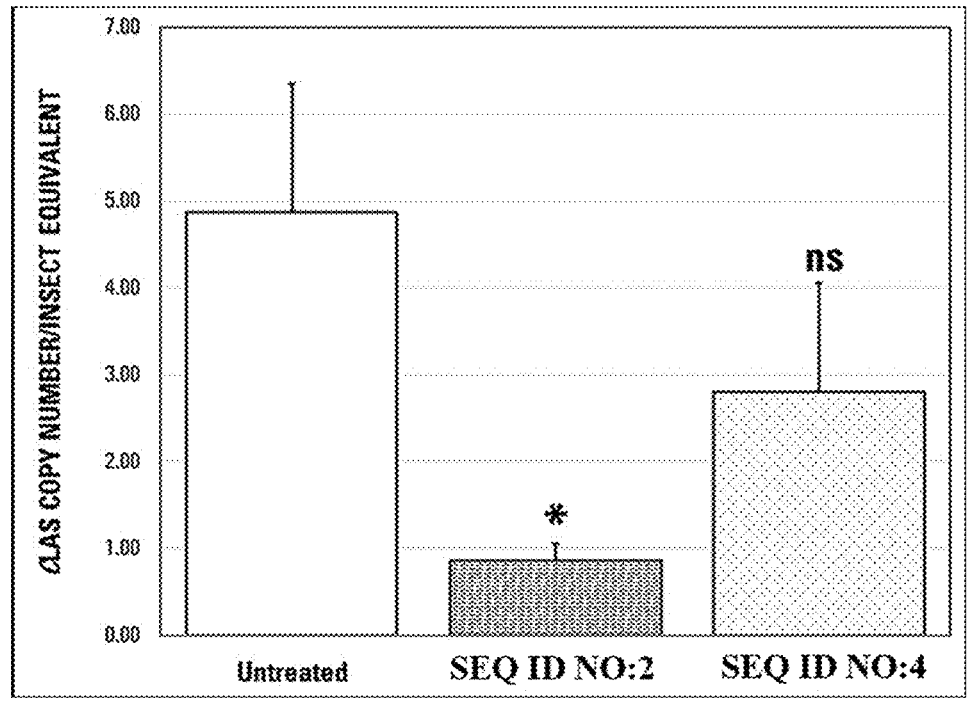
Figure 5:
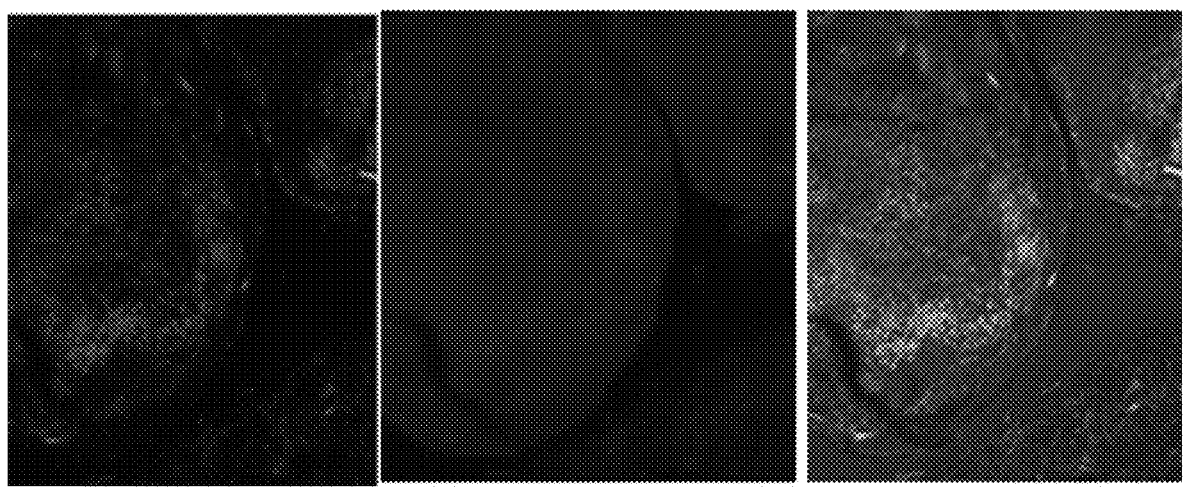
FIG. 5 provides micrographs demonstrating the detection of PPMOs in glassy-winged sharpshooter testis tissue following ingestion of root-treated citrus. 12d post feeding on PPMO treated citrus, the testis of GWSS were dissected and fixed with 3.7% paraformaldehyde and mounted on slides using a green nuclear staining solution. Tissues were viewed under confocal microscope and photographs were taken at 10× magnification showing (left to right) green fluorescence (nuclear staining), red-emitting fluorescent (lissamine-labeled PPMO), and overlapping fluorescence.

The bactericidal effect of PPMOs was tested by quantifying CLas relative density in *D. citri* aduts, after feeding psyllids with a solution containing PPMOs of SEQ ID NO:2 or SEQ ID NO:4 for seven days. Although the overall comparison between the treatments did not find significant difference among means (F [2, 24]=3.173, p=0.059), the Dunnett's test showed a significant 82% reduction of CLas titer in adult psyllids that were treated with SEQ ID NO:2, compared to untreated insects (FIG. 4B). No difference in CLas density was observed between *D. citri* adults exposed to the SEQ ID NO:4 and untreated psyllids (FIG. 4B). The results showed that degrading the CLas gyrA mRNA was detrimental for the bacterium titer inside *D. citri*.

In Planta Feeding.

Citrus seedlings which previously tested positive for PPMO detection using root immersion methods were used for this bioassay. Ten psyllids were given feeding access to PPMO-treated and control untreated citrus seedlings. 14 days post start of psyllid feeding, psyllids were sacrificed for confocal microscopy preparation and analysis. Insects were punctured or bisected with a razor to allow penetration of buffers into tissue. The tissues were first fixed using a Sucrose/NaCitrate Method, then cleared using Visikol Histo™ according to manufacturer's instructions. Tissue was then prepared for Confocal Microscopy.

To test the interaction of PPMOs with microbes in psyllids via feeding, PPMOs were systemically delivered to insect tissues by feeding on PPMO-treated citrus (soil-applied PPMOs).

Figure 12:
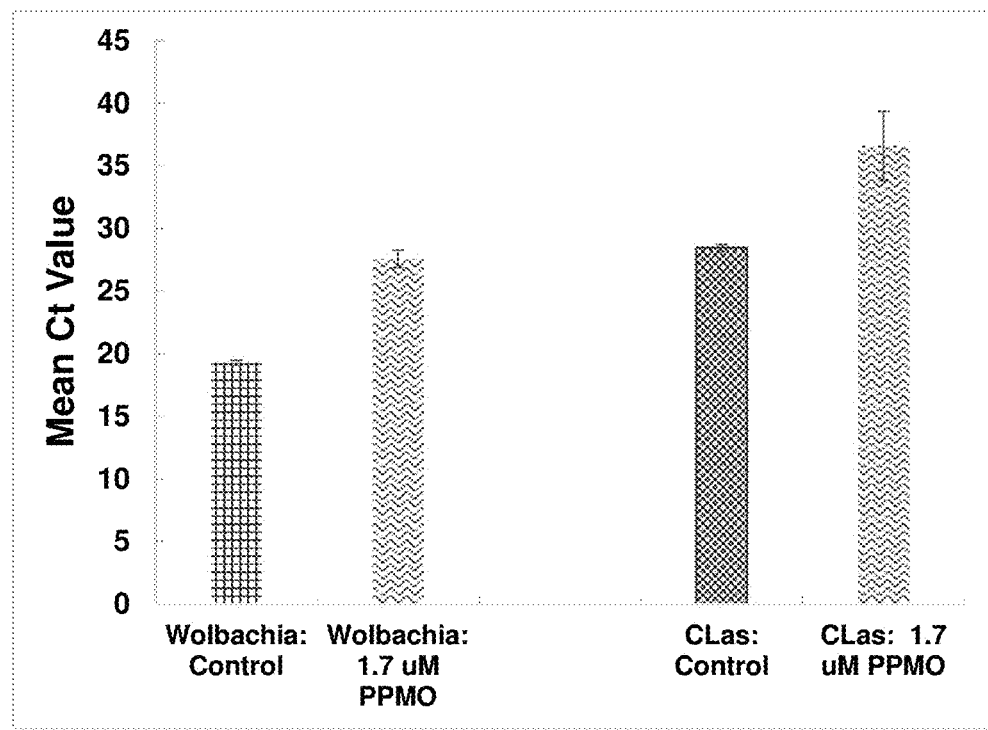

Infected citrus seedling trees were validated for CLas-infection using previously described methods. Psyllid adults reared on these plants were used for analyses. A trial using 20 adult psyllids (*D. citri*) per tree, were given a feeding access period of 8 days on CLas-infected citrus seedling trees. DNA was extracted from Psyllids feeding from Control (water) and PPMO treatments. Three citrus seedlings (sweet orange) per treatment were utilized. Using standard methods and a DNA concentration/volume of 4 ng/μL nucleic acid qPCR reactions for *Wolbachia*-Dc were run. Low range PPMO concentration (0.5 μM), showed no significant differences. A 'High Range' of PPMO concentration for significant activity was determined to be 1.7 μM PPMO which was used for analyses (FIG. 12). PPMOs utilized were SEQ ID NO:6 and SEQ ID NO:7. The PPMO treatment concentration was also used for analyses of Wolb-Dc and CLas binding assays in the CLas infected citrus seedling trees.

For CLas analyses, DNA concentration per volume was 20 ng/μL nucleic acid used for each CLas qPCR reactions.

Again, the Low range PPMO concentration of 0.5 µM, resulted in no significant differences, and the previously determined concentration of PPMO of 1.7 µM was used for comparative analyses as shown in (FIG. 12). The feeding assays were performed at room temp (20-23 C±3° C.) under artificial lighting set at 16:8 h light:dark cycle, and 60-65% relative humidity.

DNA Extraction

Total nucleic acids were extracted from excised petiole and midribs of citrus leaves positive for CLas using a DNeasy Plant Mini Kit (Qiagen). Twenty adult Asian citrus psyllid (*D. citri*) were obtained from the USDA-ARS insectary (Ft. Pierce, Fla.) and given an 8 d feeding access on each treatment (Control or PPMO-treated plants). Collected psyllids were homogenized in 400 µL of nuclease free water. Total nucleic acids were extracted from the homogenate using a Quick-DNA™ Universal Microprep Kit (Zymo Research). Nucleic acids were quantified using a NanoDrop (ND8000). (Andrade & Hunter, 2017; Andrade et al, Sci. Rep. (2016) 6, 38082; Doi:10.1038/srep38082).

PCR

Aliquots of total nucleic acids from HLB positive leaf tissue and *D. citri* were individually used to validate the CLasP1, CLasP2, WolbP1 and ProfP1 primer sets. Each reaction consisted of 1 µL total nucleic acids, 0.5 µL of 10 µM of each primer, and 23 µL Platinum® PCR SuperMix (Invitrogen). PCR was performed in an MJ Research Peltier Thermalcycler using the following parameters: 3 min at 92° C., followed by 45 cycles of 30 s at 92° C., 30 s at 60°, and 30 s at 72° C., and a single final cycle of 72° C. for 10 min. All PCR reactions were performed in technical replicates. 10 µL of each replicate was fractionated by electrophoresis for 45 min in a 2% agarose gel stained with ethidium bromide.

qPCR

Efficacy of target binding was analyzed by quantitative PCR. Each sample was analyzed in three replicate reactions that consisted of 1 µL sample, 0.5 µL of 10 µM of each primer, 1 µL ROX reference dye (diluted 1:10), 12.5 µL Platinum® SYBR® Green qPCR SuperMix-UDG, and 9.5 µL of nuclease free water. Quantitative PCR was performed in an Applied Biosystems 7500 Real-Time PCR System with the following parameters: 2 min at 50° C., 10 min at 95° C., followed by 40 cycles of 15 s at 95° C. and 60 s at 60° C. Melting curve analysis was also obtained following completion of the final cycle.

Results

*Wolbachia* cell number reduction in *D. citri* by PPMO (SEQ ID NO:7) treatment in adult psyllid was confirmed. Analyses using qPCR showed a significant difference in Ct change of approximately 8.1 Ct values, or about 2.42-fold increase in dead *Wolbachia* in the PPMO-treated group (2,500 genome equivalents) compared to the water control treatment (500,000 genome equivalents), representing a 99.5% reduction.

The CLas cell number reduction by PPMO (SEQ ID NO:6) treatment in adult psyllids was also confirmed. Results showed a difference in Ct change was about 8.6, producing a 2.61-fold change of increase in dead CLas in the PPMO treatment (2.5 genome equivalents) as compared to the water control treatment (2,500 CLas genome equivalents). This is a reduction of 2,497.5 CLas copies in the PPMO-CLas treatment, representing a 99.9% reduction.

Delivery to Glassy-Winged Sharpshooter (*Homalodisca vitripennis*).

Citrus seedlings which previously tested positive for detection of PPMO (SEQ ID NO:6) were transplanted into 1-gallon pots. Two PPMO-treated seedlings and one control seedling were placed in insect cages in a climate controlled portable greenhouse. Ten glassy-winged sharpshooters were placed in each cage and allowed 12 d of feeding access. Two insects from each treated group were sacrificed, dissected, and prepared for confocal microscopy using insect clearing methods as described above.

Confocal microscopy of cleared tissue was also used to determine delivery. Strong signals from green nuclear staining found in the testis indicate the presence of sperm bundles. Lissamine-labeled PPMO was detected in male testes of glassy-winged sharpshooter which fed on root treated citrus indicated by the red signal. Overlapping green and red signals suggest localization of PPMO within both sperm and the surrounding gametic tissue. PPMO signal was detected throughout the testes as indicated by a deep scan of the treated tissue (FIG. 5). Detection of PPMO signals was also noted in nerve, muscle, digestive, reproductive and eye tissues in both Asian citrus psyllids and potato psyllids, leafhoppers and weevils fed on PPMO-containing plants (data not shown).

Delivery to Glassy-Winged Sharpshooter (*Homalodisca vitripennis*) in Potato.

Single glassy-winged sharpshooter (GWSS) adult and nymphs (eight control and nine treated) were collected from potato cuttings [(*Solanum tuberosum*) "Yukon Gold"] placed in 1 mL (9.3 nmol PPMO/mL) and then moved to water for duration of experiment. PPMOs tested were SEQ ID NO:21, SEQ ID NO:22, and SEQ ID NO:45. GWSS fed for approximately seven days and were collected in individual Eppendorf tubes. GWSS were immediately homogenized in 400 μL TRI reagent. A Zymo Research Direct-Zol RNA MicroPrep kit was used to extract total RNA from each individual insect. PCR analyses used 50 ng/μL of RNA template.

Samples were analyzed using qPCR as described. A 2.25-fold decrease in the leafhopper endosymbiont *Baumania* gyrA expression; across nymphs and adults (p=0.045) for each targeted region (SEQ ID NO: 21, SEQ ID NO:22). No significant change was observed in the endosymbiont *Wolbachia* gyrA expression (SEQ ID NO:45).

Delivery to Glassy-Winged Sharpshooter (*H. vitripennis*) in Okra.

Single GWSS adult and nymphs (nine control and fourteen treated); adults (nine control and eleven treated) were collected from potted okra plants root drenched with (200 nmol PPMO/mL). PPMOs tested were SEQ ID NO:5, SEQ ID NO:21, SEQ ID NO:22, and SEQ ID NO:45. GWSS fed for approximately eight days and were collected in individual Eppendorf tubes. GWSS were immediately homogenized in 400 μL TRI reagent. A Zymo Research Direct-Zol RNA MicroPrep kit was used to extract total RNA from each insect. Used 50 ng/μL of RNA template.

Nucleic acid extractions and qPCR analyses were conducted as previously described. Individuals were processed and loaded into plates as triplicates. Results showed a 4.3-fold decrease in *Baumania* gyrA expression; (p=0.044) in second and third instar GWSS. Adult GWSS feeding resulted in a 1.5-fold decrease in *Baumania* gyrA expression (p=0.045) using a PPMO of SEQ ID NO:21. Analyses of *Wolbachia* gyrA expression showed a 13.7-fold decrease in the gyrA expression (p=0.042) in the second and third instars GWSS, using a PPMO of SEQ ID NO:45. No detection of *Xylella fastidiosa* was observed in leafhoppers feeding on okra using SEQ ID NO:5.

*Diaprepes abbreviatus* Larval Feeding Assay.

*D. abbreviatus* root weevil ("DRW") larvae (9 wks old) were obtained from the insectary-USDA-ARS. A small amount of diet was added to an empty container and treated with 2 µL of PPMO (SEQ ID NO:6) solution (4.03 nmoles). Larva were given feeding access until almost all diet was consumed (3 wks). Untreated artificial diet was then added and larvae were sacrificed 13 weeks post start of treatment for microplate detection and 15 wks post treatment for confocal microscopy. Weevil larvae which fed on PPMO treated diets had significantly higher microplate readings in the 570-610 wavelength region compared to the larvae which were fed untreated diets 13 wks post feeding access (Table 3).

TABLE 3

PPMO delivery to feeding larvae (microplate results)

| Wavelength | PPMO diet | Control diet | PPMO solution (+cont) | Water only (−cont) |
| --- | --- | --- | --- | --- |
| 570 | 4722 | 1626 | 12179 | 68 |
| 580 | 5065 | 1671 | 13948 | 58 |
| 590 | 5073 | 1731 | 28259 | 55 |
| 600 | 5043 | 1689 | 29553 | 59 |
| 610 | 4519 | 1567 | 42510 | 31 |

This demonstrates successful delivery of PPMOs to DRW larval tissues per os and confocal microscopy analysis shows that PPMOs can persist post ingestion for at least three months (FIG. 6A and FIG. 6B—image from 15 weeks (105 days) post-feeding). Imaging of larval mid-gut tissue dissected from control larvae revealed strong red signal only within the nucleus due to propidium iodine staining. Whereas, imaging of mid-gut dissected from larvae fed PPMO treated diet revealed red signal in both the cytoplasm and the nucleus (FIG. 6 and FIG. 6). These results demonstrate successful intracellular delivery of PPMOs to larval mid-gut tissues and persistence of these molecules in mid-gut tissue for more than three months and the potential for long-term targeting of insects and bacteria.

Example 5

Targeting Bacteria in Insects
In Vitro Analysis:

Two gyrA targets occur in the stretch of genomic DNA that encodes the transcript of DNA gyrase subunit A in the GWSS endosymbiont, *Baumannia cicadellinicola* were targeted. The PPMO for target 1 (SEQ ID NO:21) contained three residue differences from the target and the PPMO for target 2 (SEQ ID NO:22) contained two residue differences from the target. An in vitro assay was performed by incubating isolated genomic DNA from GWSS with increasing concentrations of gyrA PPMO (SEQ ID NO:21 and SEQ ID NO:22). The relative binding efficiency was determined by real-time PCR, using primers flanking the target region to quantify amplification. A higher $C_T$ is associated with lack of amplification due to binding of morpholino. An equal increase of mean $C_T$ was observed for both targets at 0.34 µM PPMO. At 0.67 µM, target 1 amplified at a mean $C_T$ of 36.9, whereas target 2 was no longer detectable. This demonstrated that sequence identity, at the greater concentration had greater affinity and specific binding for Target 2 sequence and it was reduced or degrade with greater efficacy.

In Vivo Analysis (Feeding from Cuttings):

Single GWSS adult and nymphs were allowed 7 d of feeding access to potato cuttings which were submerged in 1 mL (9.3 nmol PPMO (SEQ ID NO:21)). Adults and nymphs fed on control and PPMO treated cuttings were then transferred to water diet only for duration of experiment. GWSS were collected in individual Eppendorf tubes. GWSS were immediately homogenized in 400 µL of TRI reagent. A Zymo Research Direct-zol RNA MicroPrep kit was used to extract total RNA from each insect. 50 ng/µL of RNA template was used for the RT-qPCR reaction. Primers were designed to detect mRNA expression of gyrase A from both species of bacteria. Two assays were performed using different plants and treatment applications. The first delivered the treatments via potato cuttings. For the first assay, results have shown a 2.25-fold decrease of *Baumannia* gyrase A expression; p=0.045. No change was shown in *Wolbachia*-Hv gyrase A expression. This includes both nymphs and adults.

Targeting the Asian Citrus Psyllid Endosymbiont, *Candidatus Proffiella Armature*

In Vivo Analysis (Feeding from Cuttings):

Citrus cuttings were washed with bleach and rinsed with DI water. Cuttings were placed into 2 mL microfuge tubes containing 0.5 mL volumes of the treatment solutions: water and PPMO. The final amount of PPMO (SEQ ID NO:4, SEQ ID NO:17, SEQ ID NO:18 and SEQ ID NO:19) in the absorption solution was 30.21 nmoles. Parafilm was wrapped around the top of the microfuge tubes. Five cuttings from each treatment group were placed into plastic 50 mL tube cages. 15 to 20 Asian citrus psyllids were introduced into each of the cages and given nine days of feeding access. Mortality was measured on days two, five, eight, and nine of feeding access. Live psyllids were sacrificed on day nine of feeding by placing the cages in the ultralow temperature freezer set at −80 degrees. Single psyllids were transferred from each cage of their respective treatment groups.

Figure 7:
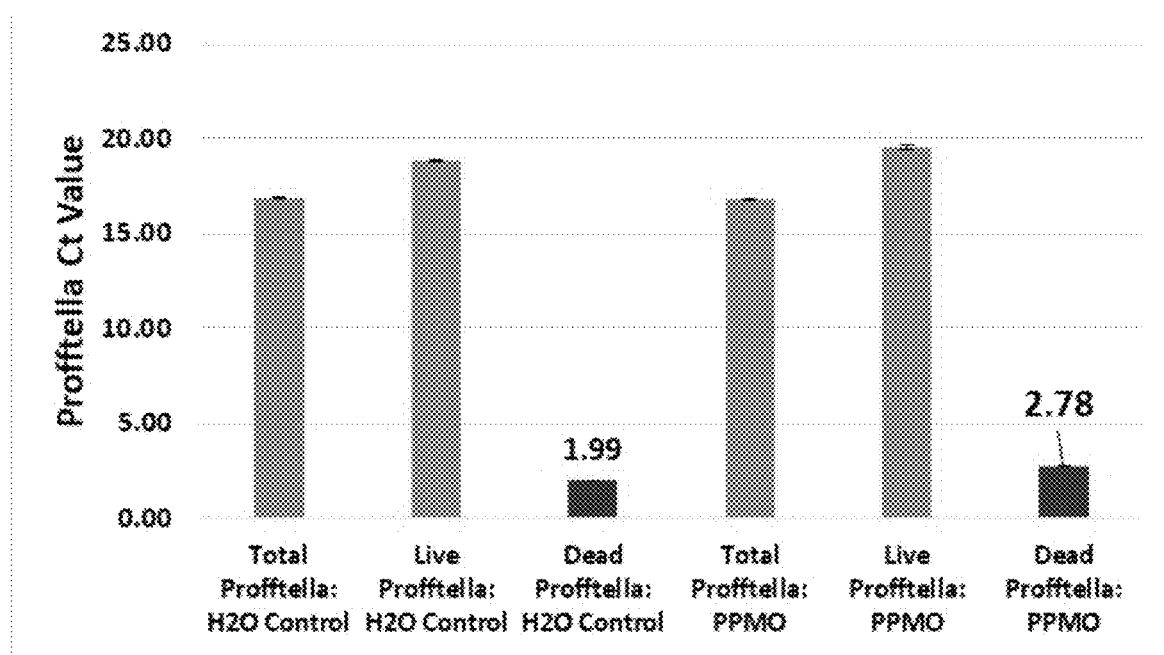
FIG. 7 provides a graphic representation of the bacteria-killing effects of PPMOs delivered via insect feeding on PPMO-containing plant material.

Single psyllid samples were homogenized in 2 mL micro centrifuge tubes containing 100 µL of nuclease free water using RNase-free disposable plastic pellet pestles. 50 µL of nuclease free water was added to bring the final volume in each tube to 150 uL. After mixing the contents by vortexing, the volume was split in half and transferred to two new 1.5 mL centrifuge tubes. Using a method previously described for quantification of bacteria, propidium monoazide (PMA) was added to one of the two vials from each psyllid sample (Hu et al, Plant Dis., (2013) 97:115-67). Samples with PMA were incubated for 5 minutes on ice and inverted three times during incubation and exposed to intense light for 5 minutes. All samples were then extracted using a DNeasy Blood & Tissue kit following the manufacturer's protocols. The elution volume was 40 µL of nuclease free water. Extracted samples were quantified using NANODROP8000 and normalized for qPCR. The qPCR mix was 12.5 µL of SYBR green master mix, 1 µL of forward primer and 1 µL of reverse primer corresponding to *Candidatus Proffiella*, 1 µL of ROX dye, approximately 8 ng of extracted DNA, and 9 µL of nuclease free water. The qPCR conditions were one cycle of 95° C. for 10 min, 40 cycles of 95° C. for 15 s and 60° C. for 30 s according to previously developed methods (Chu et al, Microb. Ecol., (2016) 71:999-1007). Results are shown in FIG. 7. This results in a $C_T$ change of 0.79 and indicating PPMOs can be used to target and kill bacteria inside feeding insects.

Figure 8:
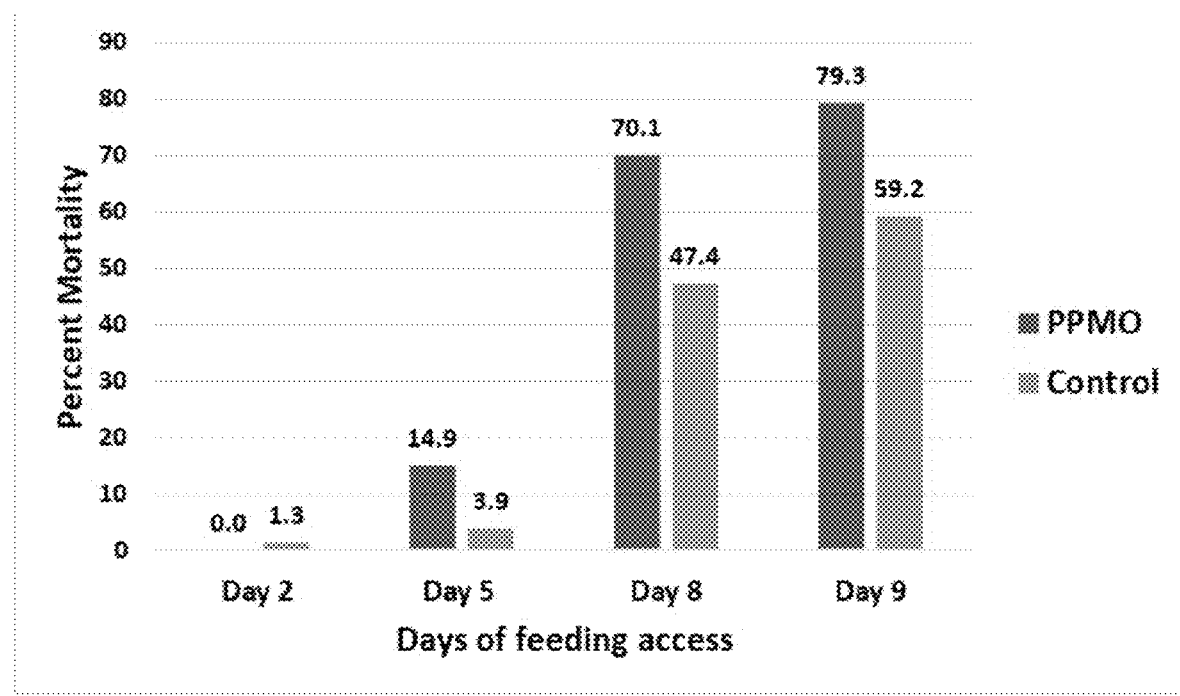
FIG. 8 provides a graphic representation of the increased mortality in Asian citrus psyllids feeding on plants containing PPMOs targeting a bacterial endosymbiont.
Figure 9:
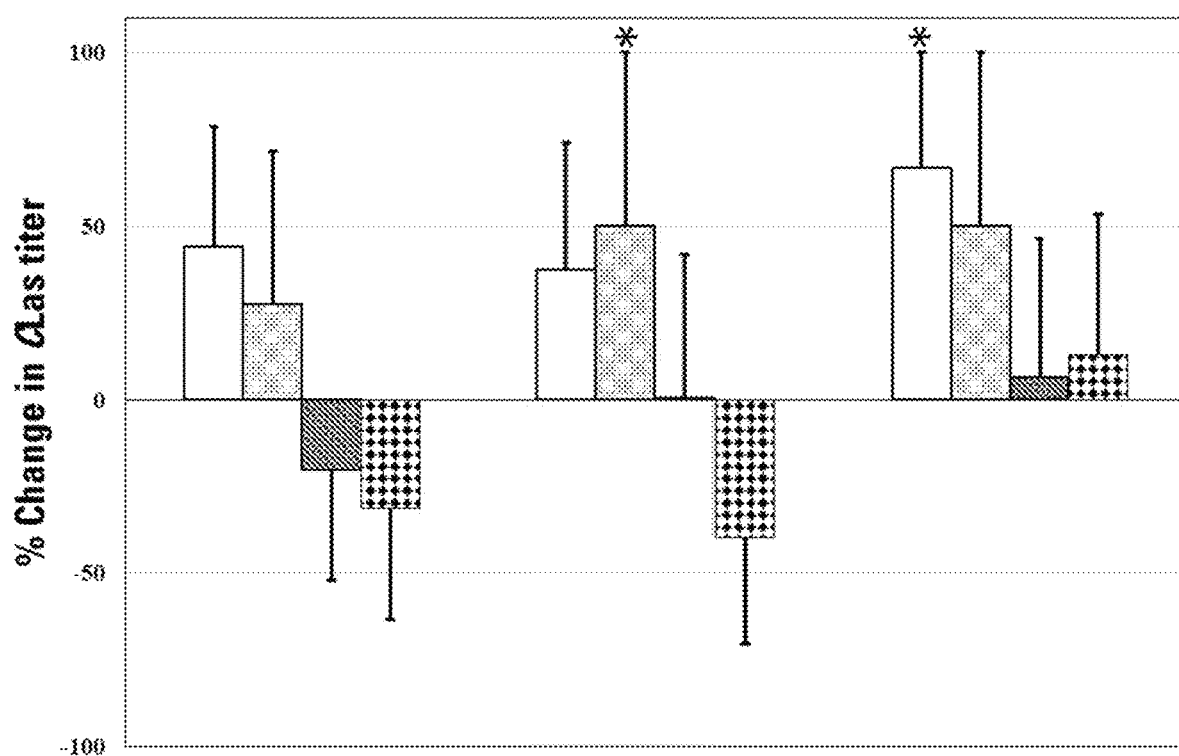
Figure 10:
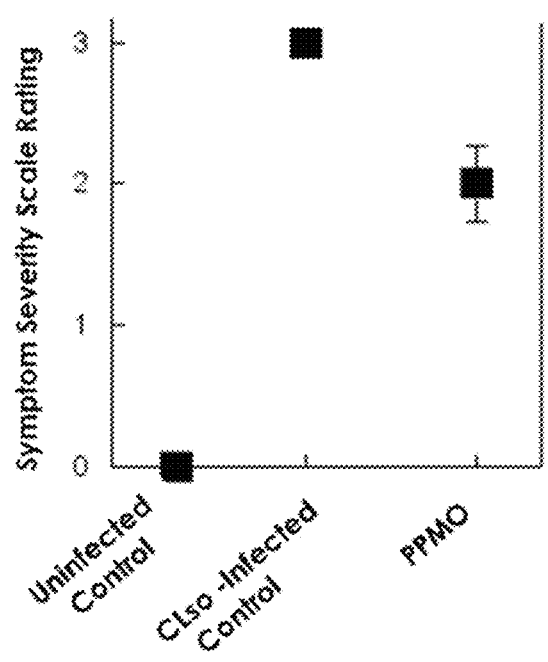
Figure 11:
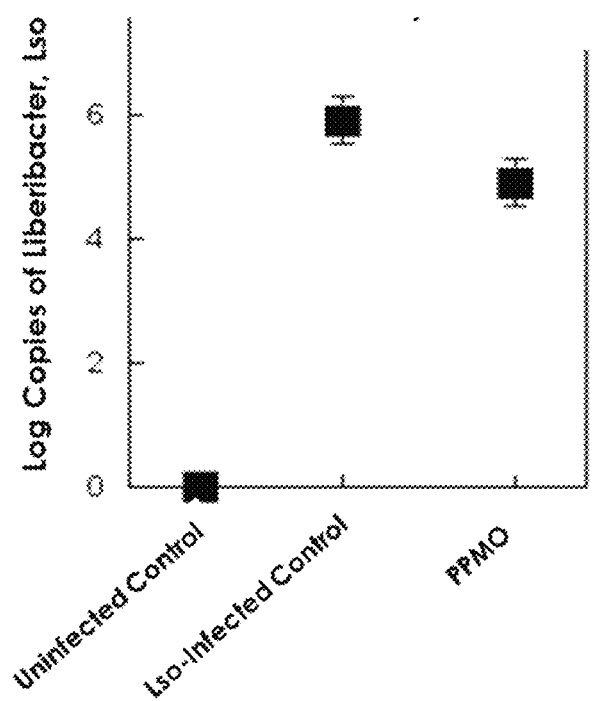

Percent mortality of the psyllids increased in cages in which the psyllids were feeding on PPMO-treated cuttings and, thus, ingesting the PPMO solution. No phytotoxicity or repellency effect was noted in either treatment group. An ANOVA single factor was performed to test the variance of the final mortalities in each treatment group. The results (FIG. 8) indicated that the differences between the means were statistically significant given that the P-value was less than 0.05 thus the null hypothesis was rejected (P-value: 0.041). The increased suppression of the bacterial endosymbiont was correlated with increased mortality of the insect.

Example 6

Targeting CLas in Citrus

Quantification of CLas in Psyllids and Plants.

Groups of 16 infected adult psyllids were fed with PPMOs of SEQ ID NO:2 or SEQ ID NO:4, using the artificial feeding system described above. CLas infected 'Pineapple' sweet orange trees grafted on 'Swingle' citrumelo rootstocks [*Citrus paradisi* MacFaden X *Poncirus trifoliate* (L.) Raf.], two to three years old, were treated with the PPMOs by root infusions. The main root system of each tree was scraped with a razor blade and fitted into a PVC tube filled with 5 mL of either a 5 μM PPMO solution (SEQ ID NO:2 or SEQ ID NO:4), a 5 mg/mL streptomycin sulfate solution (Thermo Fisher Scientific) or water (untreated control). At seven, 14- and 30-days post treatment three leaves were removed from each plant to assess the effect of PPMOs on CLas titer. The initial bacterial titer of each plant was quantified prior to the root infusions. Six trees were used per treatment.

DNA was extracted from psyllid and leaf samples as described in Pelz-Stelinski et al. (2010) (supra) and diluted to 50 ng $\mu L^{-1}$ and 15 ng $\mu L^{-1}$, correspondingly. A multiplex TaqMan qPCR assay was performed using probe and primers targeting CLas 16S rRNA gene; *D. citri* wingless (Wg) gene and the citrus mitochondrial cytochrome oxidase gene (Cox) were used as internal control for DNA extractions. All qPCR reactions were performed on a QuantStudio 6 Flex Real-Time PCR Instrument (Thermo Fisher Scientific) using the PerfeCTa® qPCR ToughMix, Low ROX (Quanta BioSciences, Gaithersburg, Md.). CLas copy number was quantified as formerly reported (Chu et al., 2016). The standard curves obtained for CLas in the insect and plant experiments were $\leq y=-3.286x+10.338$; $R^2=0.99$ and $y=-3.312x+11.763$; $R^2=0.99$, respectively.

For the psyllid assays, CLas copy number was divided by the Wg gene copy number in the same sample. One-way analysis of variance (ANOVA) was used to evaluate the differences in CLas copy number between the treatments. Control and treatment means were calculated and compared by Dunnett's test. P-values less than 0.05 were considered statistically significant. In the plant experiments, the treatments effect was expressed as percent change in CLas titer [(mean titer after treatment—mean titer prior to treatment)/mean titer prior to treatment]×100 (Hu et al., 2018). One-way analysis of variance (ANOVA) was used to compare the plants initial and final CLas copy number within the treatments. The mean of each experimental group was compared to the control group mean by Dunnett's test, considering P-values equal or less than 0.05 as statistically significant. The statistical analyses were performed using the software STATISTICA 13.3 (TIBCO Software) and GraphPad Prism (GraphPad Software).

The efficacy of PPMOs in suppressing CLas titer in Citrus plants, was tested by delivering the oligos through root infusions into trees harboring the bacterium. Though no statistical differences were detected (Dunnett's test, $p>0.05$), the plants treated with the PPMOs showed a reduction in CLas titer compared to controls (FIG. 9). Two days post-treatment, whereas water-infused and streptomycin-infused trees had 44.2 and 27.5% increase in CLas titer, the trees exposed to SEQ ID NO:2 or SEQ ID NO:4 decreased CLas density by 20.2 and 31.3%, respectively; seven days post-treatment, SEQ ID NO:4-treated plants lowered CLas titer by 40%, whereas plants infused with water or streptomycin increased CLas titer by 37.4 and 50%, correspondingly. No pathogen suppression was observed in PPMOs-treated plants 14 days post-treatment (FIG. 9).

Example 7

Targeting CLso in Potatoes

Similarly to ACP transmission of CLas in citrus, potato psyllids transmit *Candidatus Liberibacter solanacearum* (CLso) in potatoes. For these studies, PPMO (SEQ ID NO:8) was applied to potted CLso-infected potato plants (Russett variety) Psyllid transmitted Lso into potato (Russett variety). PPMO (conc. 500 nM) was applied as a soil treatment of 100 mL solution of water applied as two doses, 2 weeks apart. A water-only non-infected group, and a water-only CLso infected group were included as controls. Each group consisted of five (5) plants. A visual score and qPCR analyses were performed at 5 weeks post second treatment. PPMO treated plants were healthier on visual score analysis than the infected treatment controls, but less healthy than uninfected control plants (FIG. 10). Psyllids feeding on PPMO-containing plants also showed a decrease in CLso titer (FIG. 11).

While the invention has been described with reference to details of the illustrated embodiments, these details are not intended to limit the scope of the invention as defined in the appended claims. The embodiment of the invention in which exclusive property or privilege is claimed is defined as follows:

What is claimed is:

1. An oligonucleotide comprising at least one phosphorodiamidate morpholino residue, the oligonucleotide having a sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, and SEQ ID NO:49.

2. The oligonucleotide of claim 1, wherein each residue of the oligonucleotide comprises a phosphorodiamidate morpholino residue.

3. The oligonucleotide of claim 1 or claim 2, further comprising a peptide conjugated to the oligonucleotide.

4. A method of controlling bacteria present in an insect, comprising the steps of:
   a. contacting a food source edible by the insect with an oligonucleotide comprising at least one phosphorodiamidate morpholino residue, wherein the oligonucleotide comprises a sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, and SEQ ID NO:49;
   b. allowing the insect to feed on the food source, thereby ingesting the oligonucleotide; and
   c. inducing RNA silencing in at least some of the bacteria present in the insect, thereby controlling the bacteria.

5. The oligonucleotide of claim 4, wherein each residue of the oligonucleotide comprises a phosphorodiamidate morpholino residue.

6. The method of claim 4, wherein the bacteria is *Candidatus Liberibacter asiaticus* or *Candidatus Liberibacter solanacearum*.

7. The method of claim 4, wherein the food source is a plant, a bait material, an artificial diet, or a sugar solution.

8. The method of claim 7, wherein the food source is a plant and the oligonucleotide is contacted with the plant by root soak, injection or foliar spray.

9. The method of claim 4, wherein the food source is a citrus plant.

10. The method of claim 4, wherein the insect is *Diaphorina citri* or *Diaprepes abbreviatus*.

11. A method of controlling a bacterium, wherein the bacterium is a plant pathogen present in plant tissues, comprising the steps of:
    a. contacting the plant with an oligonucleotide, wherein the oligonucleotide is selected from the group consisting and having SEQ ID NO:2, SEQ ID NO:5, SEQ ID NO:6, SEQ ID NO:8, SEQ ID NO:9, SEQ ID NO:10, SEQ ID NO:11, SEQ ID NO:12, SEQ ID NO:23, SEQ ID NO:24, SEQ ID NO:25, SEQ ID NO:26, SEQ ID NO:41, SEQ ID NO:42, SEQ ID NO:43, SEQ ID NO:44, SEQ ID NO:46, SEQ ID NO:47, SEQ ID NO:48, and SEQ ID NO:49 and wherein the oligonucleotide comprises at least one oligonucleotide comprising at least one phosphorodiamidate morpholino residue in a manner whereby the oligonucleotide distributes through at least some of the plant tissues, thereby providing the oligonucleotide to the bacterium; and
    b. contacting the oligonucleotide with the bacterium, thereby inducing a detrimental effect to the bacterium.

12. The method of claim 11, wherein the bacterium is *Candidatus Liberibacter asiaticus* or *Candidatus Liberibacter solanacearum*.

13. The method of claim 11, wherein the oligonucleotide is contacted with the plant by root soak, injection or foliar spray.

14. The method of claim 11, wherein the plant is citrus or potato.

15. An oligonucleotide comprising at least one phosphorodiamidate morpholino residue, the oligonucleotide comprising SEQ ID NO: 21 and a peptide conjugated to the oligonucleotide.

* * * * *